United States Patent
Lidaka et al.

(10) Patent No.: US 12,167,081 B2
(45) Date of Patent: Dec. 10, 2024

(54) METHODS AND SYSTEMS FOR PERSONALIZED CONTENT BASED ON CAPTURED GESTURES

(71) Applicant: Adeia Guides Inc., San Jose, CA (US)

(72) Inventors: Christopher Charles Lidaka, Apex, NC (US); Reda Harb, Bellevue, WA (US)

(73) Assignee: Adeia Guides, Inc., San Jose, CA (US)

( * ) Notice: Subject to any disclaimer, the term of this patent is extended or adjusted under 35 U.S.C. 154(b) by 0 days.

(21) Appl. No.: 17/326,593

(22) Filed: May 21, 2021

(65) Prior Publication Data
US 2022/0377413 A1    Nov. 24, 2022

(51) Int. Cl.
| | |
|---|---|
| H04N 21/442 | (2011.01) |
| G06F 3/01 | (2006.01) |
| G06V 40/10 | (2022.01) |
| G06V 40/20 | (2022.01) |
| H04N 21/258 | (2011.01) |
| H04N 21/472 | (2011.01) |

(52) U.S. Cl.
CPC ....... *H04N 21/44218* (2013.01); *G06F 3/017* (2013.01); *G06V 40/107* (2022.01); *G06V 40/28* (2022.01); *H04N 21/25891* (2013.01); *H04N 21/472* (2013.01)

(58) Field of Classification Search
CPC ....... H04N 21/44218; H04N 21/25891; H04N 21/472; H04N 21/4223; H04N 21/4756; H04N 21/4826; H04N 21/84; G06F 3/017; G06V 40/107; G06V 40/28; G06V 40/16; A61B 5/11; A61B 5/6898; H04H 60/46; H04H 60/65; H04H 60/33
See application file for complete search history.

(56) References Cited

U.S. PATENT DOCUMENTS

| | | | |
|---|---|---|---|
| 7,836,467 B2 * | 11/2010 | Gordon | H04N 21/23614 725/39 |
| 7,934,170 B2 * | 4/2011 | Fulcher | H04N 21/632 715/846 |
| 7,962,935 B2 * | 6/2011 | Kurosaki | H04H 20/76 725/39 |
| 8,327,395 B2 * | 12/2012 | Lee | H04N 21/6582 725/10 |

(Continued)

FOREIGN PATENT DOCUMENTS

WO    WO-2018084854 A1 *    5/2018    ............ H04W 4/023

*Primary Examiner* — An Son P Huynh
(74) *Attorney, Agent, or Firm* — Haley Guiliano LLP

(57) ABSTRACT

Systems and methods are presented for providing personalized content based on gestures, in order to provide a seamless and user-driven feedback capture platform that captures user gestures and provides improved personalized content. The system captures biometric data from the user during the presentation of a first content item from a first content source. The system identifies the feedback indicator from the biometric data captured during the output of the first content item and stores an identifier of the second content item associated with the first content item in the master list. The system generates the master list for display and, in response to receiving a selection of the identifier of the second content item, retrieves for output the second content item from the second content source on the user device.

18 Claims, 10 Drawing Sheets

(56) References Cited

U.S. PATENT DOCUMENTS

| | | | |
|---|---|---|---|
| 8,667,519 B2* | 3/2014 | Small | H04N 21/44218 725/86 |
| 8,793,736 B2* | 7/2014 | Kueh | H04N 21/4821 725/38 |
| 8,806,536 B2* | 8/2014 | Ellis | H04N 21/4755 725/40 |
| 8,898,687 B2* | 11/2014 | Hulten | H04N 21/442 725/12 |
| 9,137,558 B2* | 9/2015 | Gibbon | H04H 60/43 |
| 9,342,846 B2* | 5/2016 | Maddali | G06F 40/30 |
| 9,538,219 B2* | 1/2017 | Sakata | H04N 21/25891 |
| 10,134,048 B2* | 11/2018 | Deephanphongs | G06Q 30/0201 |
| 10,149,008 B1* | 12/2018 | Logan | H04N 21/44218 |
| 10,187,690 B1* | 1/2019 | Garcia | H04N 21/44226 |
| 10,187,694 B2* | 1/2019 | Meredith | H04H 60/66 |
| 10,225,608 B2* | 3/2019 | Shigeta | H04N 21/42203 |
| 10,304,346 B2* | 5/2019 | Peterson | G09B 5/00 |
| 10,349,090 B2* | 7/2019 | Mateik | H04N 21/4826 |
| 10,394,408 B1* | 8/2019 | Freund | H04N 21/00 |
| 10,587,921 B2* | 3/2020 | Cho | H04N 21/44204 |
| 10,721,705 B1* | 7/2020 | Kerr | H04W 4/02 |
| 10,779,016 B2* | 9/2020 | Newell | H04N 21/41407 |
| 10,798,451 B2* | 10/2020 | Wilkinson | H04N 21/44218 |
| 10,820,060 B1* | 10/2020 | Bosworth | H04N 21/478 |
| 10,877,982 B1* | 12/2020 | De Boursetty | G06F 16/9535 |
| 10,911,829 B2* | 2/2021 | el Kaliouby | A61B 5/0077 |
| 11,056,014 B1* | 7/2021 | Chasen | G09B 7/00 |
| 11,082,467 B1* | 8/2021 | Hartnett | H04L 65/611 |
| 11,514,948 B1* | 11/2022 | Nair | H04N 7/155 |
| 11,558,672 B1* | 1/2023 | Clasen | H04N 21/61 |
| 2001/0001160 A1* | 5/2001 | Shoff | H04N 21/4312 725/108 |
| 2005/0132401 A1* | 6/2005 | Boccon-Gibod | H04N 21/8455 725/35 |
| 2009/0007200 A1* | 1/2009 | Amento | H04N 21/4788 725/100 |
| 2009/0131764 A1* | 5/2009 | Lee | A61B 5/11 600/301 |
| 2009/0133047 A1* | 5/2009 | Lee | H04N 7/16 725/10 |
| 2009/0300475 A1* | 12/2009 | Fink | H04N 21/8541 726/4 |
| 2009/0319181 A1* | 12/2009 | Khosravy | G06Q 30/02 701/532 |
| 2009/0328122 A1* | 12/2009 | Amento | A63F 13/53 725/114 |
| 2010/0043020 A1* | 2/2010 | Basso | H04N 21/6582 725/40 |
| 2011/0010307 A1* | 1/2011 | Bates | G06Q 30/02 705/26.7 |
| 2011/0069940 A1* | 3/2011 | Shimy | H04N 5/44543 386/296 |
| 2011/0138408 A1* | 6/2011 | Adimatyam | H04H 60/372 725/37 |
| 2011/0173214 A1* | 7/2011 | Karim | G06F 16/435 707/754 |
| 2011/0247044 A1* | 10/2011 | Jacoby | H04N 21/4622 725/115 |
| 2011/0283320 A1* | 11/2011 | Levin | H04N 21/252 725/40 |
| 2011/0310305 A1* | 12/2011 | Alexander | H04N 21/4667 348/725 |
| 2012/0124604 A1* | 5/2012 | Small | H04N 21/4223 725/12 |
| 2012/0278179 A1* | 11/2012 | Campbell | G06Q 30/0255 705/14.69 |
| 2012/0278331 A1* | 11/2012 | Campbell | H04N 21/44204 707/740 |
| 2013/0145385 A1* | 6/2013 | Aghajanyan | H04N 21/251 725/10 |
| 2013/0166561 A1* | 6/2013 | Georgescu | G06F 16/78 707/739 |
| 2013/0167168 A1* | 6/2013 | Ellis | H04N 21/458 725/12 |
| 2013/0173765 A1* | 7/2013 | Korbecki | H04N 21/42209 709/221 |
| 2013/0205314 A1* | 8/2013 | Ramaswamy | H04N 21/44218 725/14 |
| 2013/0212606 A1* | 8/2013 | Kannan | H04H 60/45 725/12 |
| 2013/0268955 A1* | 10/2013 | Conrad | H04N 21/8456 725/12 |
| 2013/0298146 A1* | 11/2013 | Conrad | H04N 21/44213 725/35 |
| 2013/0346867 A1* | 12/2013 | Woods | G11B 27/34 715/728 |
| 2014/0007147 A1* | 1/2014 | Anderson | H04N 21/6582 725/9 |
| 2014/0026156 A1* | 1/2014 | Deephanphongs | H04N 21/4223 725/12 |
| 2014/0068692 A1* | 3/2014 | Archibong | H04N 21/6334 725/116 |
| 2014/0081954 A1* | 3/2014 | Elizarov | H04N 21/4788 707/722 |
| 2014/0114919 A1* | 4/2014 | Woods | H04N 21/4622 707/634 |
| 2014/0168056 A1* | 6/2014 | Swaminathan | G06V 40/19 345/156 |
| 2014/0237587 A1* | 8/2014 | Forbes | G06F 21/00 726/18 |
| 2014/0365272 A1 | 12/2014 | Hurewitz | |
| 2015/0074718 A1* | 3/2015 | Moguillansky | H04N 21/26291 725/40 |
| 2015/0153910 A1* | 6/2015 | Wheeler | G06F 3/0485 715/837 |
| 2015/0350729 A1* | 12/2015 | Reynolds | H04N 21/47217 725/34 |
| 2015/0382071 A1 | 12/2015 | Aravamudan | |
| 2016/0006981 A1* | 1/2016 | Bauman | H04N 21/4788 348/14.03 |
| 2016/0021412 A1* | 1/2016 | Zito, Jr. | H04N 21/4532 725/13 |
| 2016/0055160 A1* | 2/2016 | Himel | G06F 16/248 707/728 |
| 2016/0212466 A1* | 7/2016 | Nauseef | H04N 21/4223 |
| 2016/0275833 A1* | 9/2016 | Forbes | H04N 21/4667 |
| 2016/0366203 A1* | 12/2016 | Blong | H04L 65/612 |
| 2017/0006322 A1* | 1/2017 | Dury | H04N 21/254 |
| 2017/0061528 A1* | 3/2017 | Arora | G06F 16/951 |
| 2017/0132841 A1* | 5/2017 | Morrison | G06K 9/00671 |
| 2017/0134803 A1* | 5/2017 | Shaw | H04N 21/234363 |
| 2017/0168586 A1* | 6/2017 | Sinha | G06K 9/00382 |
| 2017/0264920 A1* | 9/2017 | Mickelsen | H04N 21/4394 |
| 2017/0318019 A1* | 11/2017 | Gordon | H04L 9/3226 |
| 2018/0129378 A1* | 5/2018 | Roundtree | G06F 3/0482 |
| 2018/0192000 A1* | 7/2018 | Mercredi | G06Q 50/01 |
| 2018/0234738 A1* | 8/2018 | Sarkar | H04L 51/18 |
| 2018/0249215 A1* | 8/2018 | Wilkinson | H04N 21/44222 |
| 2019/0043493 A1 | 2/2019 | Mohajer et al. | |
| 2019/0075359 A1* | 3/2019 | Boss | H04N 21/4532 |
| 2019/0244639 A1* | 8/2019 | Benedetto | G11B 27/11 |
| 2019/0339831 A1* | 11/2019 | Kobayashi | G06F 3/0484 |
| 2020/0081591 A1* | 3/2020 | Karri | G06V 40/19 |
| 2020/0110461 A1* | 4/2020 | Trim | H04N 21/44213 |
| 2020/0111148 A1 | 4/2020 | Soni et al. | |
| 2020/0169787 A1* | 5/2020 | Pearce | G06F 16/955 |
| 2020/0184105 A1* | 6/2020 | Nikain | G06F 21/6254 |
| 2020/0273485 A1* | 8/2020 | Jagmag | G06Q 30/0631 |
| 2020/0288204 A1* | 9/2020 | Duersch | G06N 3/045 |
| 2020/0382646 A1* | 12/2020 | Rao | H04L 51/18 |
| 2020/0389757 A1* | 12/2020 | Kerr | G06Q 30/0261 |
| 2021/0037295 A1* | 2/2021 | Strickland | H04N 21/6582 |
| 2021/0049626 A1* | 2/2021 | Ishiguro | G06F 16/9538 |
| 2021/0073953 A1* | 3/2021 | Lee | G06N 3/0454 |
| 2021/0105332 A1* | 4/2021 | Bellet | G06Q 10/10 |
| 2021/0136448 A1 | 5/2021 | Ramirez et al. | |

(56) References Cited

U.S. PATENT DOCUMENTS

2021/0258643 A1* 8/2021 Park .................. H04N 21/4756
2021/0397793 A1* 12/2021 Li ........................ G06N 20/00
2022/0180186 A1* 6/2022 Basilico ................. G06N 3/08

* cited by examiner

602 Captured Feedback

| Viewer A | User Feedback | Content | Content Source |
|---|---|---|---|
| John | Thumbs Up | Ozark | Netflix |
| John | Thumbs Up | TOM CLANCY's JACK RYAN | Amazon |
| John | Thumbs Up | Handmaid Tale | Hulu |
| John | Thumbs Down | The Crown | Netflix |
| John | Thumbs Up | Happy (Song) | Spotify |
| John | Thumbs Up | Headphones | Store |

FIG. 6A

VIEWER PREFERENCES 610

| GENRES 612 | DRAMA, ROMANCE, HOLIDAY |
|---|---|
| ACTORS 614 | BRADLEY COOPER, HUGH GRANT, MERYL STREEP |
| SETTINGS 616 | LONDON, PARIS, ANCIENT EGYPT, BEACHES |
| CHARACTERS 620 | STRONG FEM. LEAD, HEALTH PROFESSIONALS, MENTORS |
| SCENES DISLIKED 630 | GUN VIOLENCE, WAR, SPIDERS/BUGS |

FIG. 6B

SCENE METADATA 670

| SCENE 671 | 034 |
|---|---|
| GENRES 672 | ACTION, SUPERHERO |
| ACTORS 674 | JOHN KRASINSKI |
| SETTINGS 676 | SPACESHIP, SPACE |
| CHARACTERS 678 | SUPERHEROES, SIDEKICKS |
| TAGS 679 | FRIENDSHIP, SPACE BATTLE |

FIG. 6C

CONTENT METADATA 640

| GENRES 642 | ACTION, DRAMA, SUPERHERO |
|---|---|
| ACTORS 644 | CHRIS PRATT, ZOE SALDANA, BRADLEY COOPER |
| SETTINGS 646 | SPACE, ALIEN PLANETS |
| CHARACTERS 648 | SUPERHEROES, STRONG FEM. LEAD, TEAM |
| THEMES 650 | TEAMWORK, FAMILY, DIVERSITY |

FIG. 6D

PRODUCT 680

| PRODUCT TYPE 681 | HEADPHONES |
|---|---|
| LABEL 683 | Boss Noise Cancelling QC35 |

FIG. 6E

AUDIO 690

| LABEL 691 | HAPPY |
|---|---|
| FEATURE 693 | POP, TOP HITS |

FIG. 6F

METHODS AND SYSTEMS FOR PERSONALIZED CONTENT BASED ON CAPTURED GESTURES

BACKGROUND

The present disclosure relates to methods and systems for providing personalized content and, more particularly, to methods and systems for providing personalized content based on captured gestures.

SUMMARY

In response to viewers' demand for more personalized content, providers have improved program content, mainly by monitoring user activities, capturing user feedback and providing more personalized content based on such activities and feedback. For example, many providers now monitor user interactions (e.g., how long they watched a movie) and feedback (e.g., a "like," a "dislike" or a "star rating") from a user using a remote control or a mobile device or another device. Another way to receive input is through gestures, for example, gestures made by the hand or face. Hand gestures may include a range of movements of the hands and fingers, where the hands may move in a linear or rotational or a combination of both movements while the individual fingers in the hand also move. Current capture engines do not capture users' feedback and integrate the data collected into an interactive presentation of content for a seamless and easier way to utilize gestures.

Another problem exists when providers (e.g., service providers, internet streamers, etc.) use the captured information to tailor the content to specific users. For example, a user providing "like" feedback on a show titled "The Bachelor" may cause the provider to suggest content related to "The Bachelor." How providers capture user feedback is limited to users providing input on a remote control, mobile phone or computer. For example, to mark content as "like" or a "dislike," the user is required to move the cursor to the upward-facing thumb or downward-facing thumb, and click the enter button, and the response is recorded on the screen. Such input is very cumbersome to enter and discourages the user from providing feedback regularly. Additionally, the combination of steps to give the input slows down the hardware executing the feedback capture.

While capturing feedback from a user has become a priority for many providers, many providers are limited to the feedback provided on their own platform. For example, one program provider, e.g., ABC, providing an advertisement for another program provider's content, e.g., a Hulu's "The Handmaid's Tale," does not permit the user to provide feedback regarding the advertisement, which results in the users to perform extra steps to generate the content for presentation. For example, in this case, the user has to manually switch from watching a program on ABC to launching the Hulu application and search for the advertised program (e.g., "The Handmaid's Tale") to generate the content for the presentation. The number of steps required to launch the content becomes tedious and takes away from the user's enjoyment while delaying content being generated for presentation. In some circumstances, the user may not remember the title of the content and may not be able to generate the content for consumption.

To solve these problems, systems and methods are disclosed herein for generating a list of content based on captured user gestures. Such systems and methods may provide a more seamless and user-driven feedback capture platform that captures user gestures and provides improved personalized content based on captured gestures, thereby simplifying steps to provide feedback, avoiding the use of a remote for entering feedback, freeing up hardware functionality by reducing the number of steps to provide feedback and generating a database for tracking and launching content for presentation.

As described below, systems and methods may include a capturing engine implemented at user equipment or a server to generate a database based on biometric data captured from a user providing user's interaction during output for consumption of a first content item (e.g., advertisement for "The Handmaid's Tale") on a first content source (e.g., "ABC") on a user device. The first content item may be an advertisement for a media asset or a product that is generated for display on the user device.

The capturing engine captures biometric data such as the user's focal point, line of sight, facial expressions, hand gestures, movements, biometric measurements, and/or the like, to determine what content (e.g., an advertisement for a content item or a product) the user is paying attention to, and whether the user likes, or dislikes the particular content item or product. In some embodiments, the captured biometric data is one or more of hand gestures of thumbs-up, thumbs-down, a heart, or a middle finger a movement of a hand in a direction, or any other combination of hand gestures with a predetermined meaning. In some embodiments, the user may customize the hand gesture and its meaning based on a template or model. For example, a tap on the head with the hand may indicate interest in the content. In other embodiments, the biometric data is the movement of one or more of a hand, a finger, an arm, a palm of a hand, a first hand or a second hand of the user.

The system may parse the biometric data to detect at least one form of biometric data to identify a feedback indicator (e.g., positive feedback or negative feedback). The feedback indicator is indicative of whether the user likes or dislikes the particular content item or product.

The system may search for a positive feedback indicator to store in a master list an identifier of the second content item. For example, an identifier of content (e.g., "The Handmaid's Tale") may be saved in a master database in response to the user's positive feedback. Upon the master list being generated for display on a user device, the user may select an identifier of the second content item (e.g., "The Handmaid's Tale") and, in response to the selection of the identifier of the second content item (e.g., "The Handmaid's Tale") from the master list, the system may cause the content source (e.g., Hulu) to launch the second content item (e.g., "The Handmaid's Tale") on the user device. In some embodiments, a first content source is any one of broadcasting stations, television stations, content on demand, the internet, or a user application. In some embodiments, a second content source is one of broadcasting stations, television stations, content on demand, the internet, or a user application, and the first content source is different from the second content source. In yet another aspect of this embodiment, the content may be selected from on demand content, recorded content or live content. In some embodiments, the content items include one or more of video content, audio content, game content, interactive content or textual content.

In some embodiments, the biometric data includes biometric measurements such as the pulse rate, blood pressure, pupil dilation, and/or the like. The capturing engine determines a change of biometric data from the biometric measurement and queries a biometric database based on the change of the biometric data to identify the emotion that is implied by the change of the biometric data.

In some embodiments, the biometric data includes a facial expression, a gesture or a body movement of the user, and/or the like. The capturing engine captures an image or video of a user's activity (including facial movement) and generates a movement pattern or facial expression pattern from the captured image or video content. The capturing engine then uses the database to identify the movement or facial expression and then identifies an emotion associated with the identified activity, e.g., whether the user likes or dislikes the particular content or product.

In some embodiments, the capturing engine may include a camera to capture the user's actions. In some embodiments, the capturing engine may include a depth camera configured to capture a depth map of the proximity of the user device to identify the form of biometric data during output for consumption of the first content item. In some embodiments, the depth camera may identify from the depth map the feedback indicator indicative of user intent—for example, a user providing a thumbs-up or thumbs-down while content is presented for consumption. The system may identify a product while capturing the biometric data (e.g., thumbs-up or thumbs-down) and add the product to a shopping list. For example, as a commercial for a product (e.g., sunglasses) is playing on the display, the user provides a thumbs-up (e.g., an indication that the user likes the sunglasses), and the system adds the sunglasses to a shopping list from any one or the user's preferred merchants.

In some embodiments, in response to identifying the feedback indicator of the first biometric data, the system may generate a plurality of segments from the first content item. Each segment is associated with metadata that identifies a content type and an identifier of the segment. In some embodiments, the system may generate for display a notification to provide additional feedback. In some embodiments, a user device (e.g., television) may generate a confirmation (e.g., user is renting or purchasing) a purchase or rental of a content item (e.g., the show "Ozark) associated with the first content item 103 (e.g., an advertisement for a show titled "Ozark"). For example, the user may want to purchase or rent the show "Ozark" that is being advertised. In response to the requested confirmation, the user device may capture hand gestures from the consumer to accept or reject the purchase. In another embodiments, the user device (e.g., television) may generate notification related to products from the first content item. For example, if there are a number of products being advertised, the system may require specific details about which product the user is providing feedback on. Alternatively, the feedback may be directed at a variation (e.g., a color or size) of the product. In some embodiments, in response to generating for display the notification, the system may capture, via the sensor (e.g., high-depth camera), at least one form of a second biometric data during output for consumption of a segment of the plurality of segments of the first content item on the user device. In some embodiments, the system by control circuitry parses the second biometric data to detect at least one form of second biometric data to identify a feedback indicator for the segment of the plurality of segments. In response to identifying that the second feedback indicator is positive, the system stores in a master list the identifier of the segment of the plurality of segments of the first content item.

Devices facilitate the delivery of content for consumption at any time and nearly in any place, which may decrease tolerance for content falling outside of a consumer's usual preferences. The ability of devices to provide content to a content consumer is often enhanced with advanced hardware with increased memory and faster processors in devices. Devices, such as computers, telephones, smartphones, tablets, smartwatches, speakers/microphones (e.g., with virtual assistants), activity trackers, e-readers, voice-controlled devices, servers, televisions, digital content systems, video game consoles, and other internet-enabled appliances can provide and deliver content almost instantly.

Content delivery systems may use, for example, interactive content guidance applications to facilitate the content selection. Typically, consumer preferences are associated with a profile or an account, such as a consumer profile, user profile, user account, subscriber profile, or subscriber account. As used herein, the term "consumer" may refer to an individual or may be used as an equivalent of a user account, subscriber account, viewer account or other accounts with content provider systems and/or services. The term "consumer" may be used interchangeably with "user" and "viewer." Preferences (based on user feedback) may be stored as part of a user profile and may be referred to as a consumer profile. A consumer profile may be stored in the cloud (e.g., a remote-secure server) and accessed by interactive content guidance applications initiated by a viewer (e.g., by logging in).

In some embodiments, the second content item is a product, and the system retrieves product information associated with the product. In some embodiments, in response to determining, based on the at least one form of biometric data, that the feedback indicator is positive towards the product, the system may add the product information to a shopping list for purchase.

In some embodiments, the system may utilize a machine learning model to learn the user's tendencies of hand gestures in order to be able to determine the user's feedback. The system may use a machine learning model to determine the intent of the user based on a hand gesture during output for consumption of the first content item and, responsive to the determined intent, cause the content source to launch the second content item on the user device.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIGS. 6A-F depict illustrative examples of a database of feedback based on captured gestures, in accordance with some embodiments of the disclosure;

DETAILED DESCRIPTION

Figure 1:
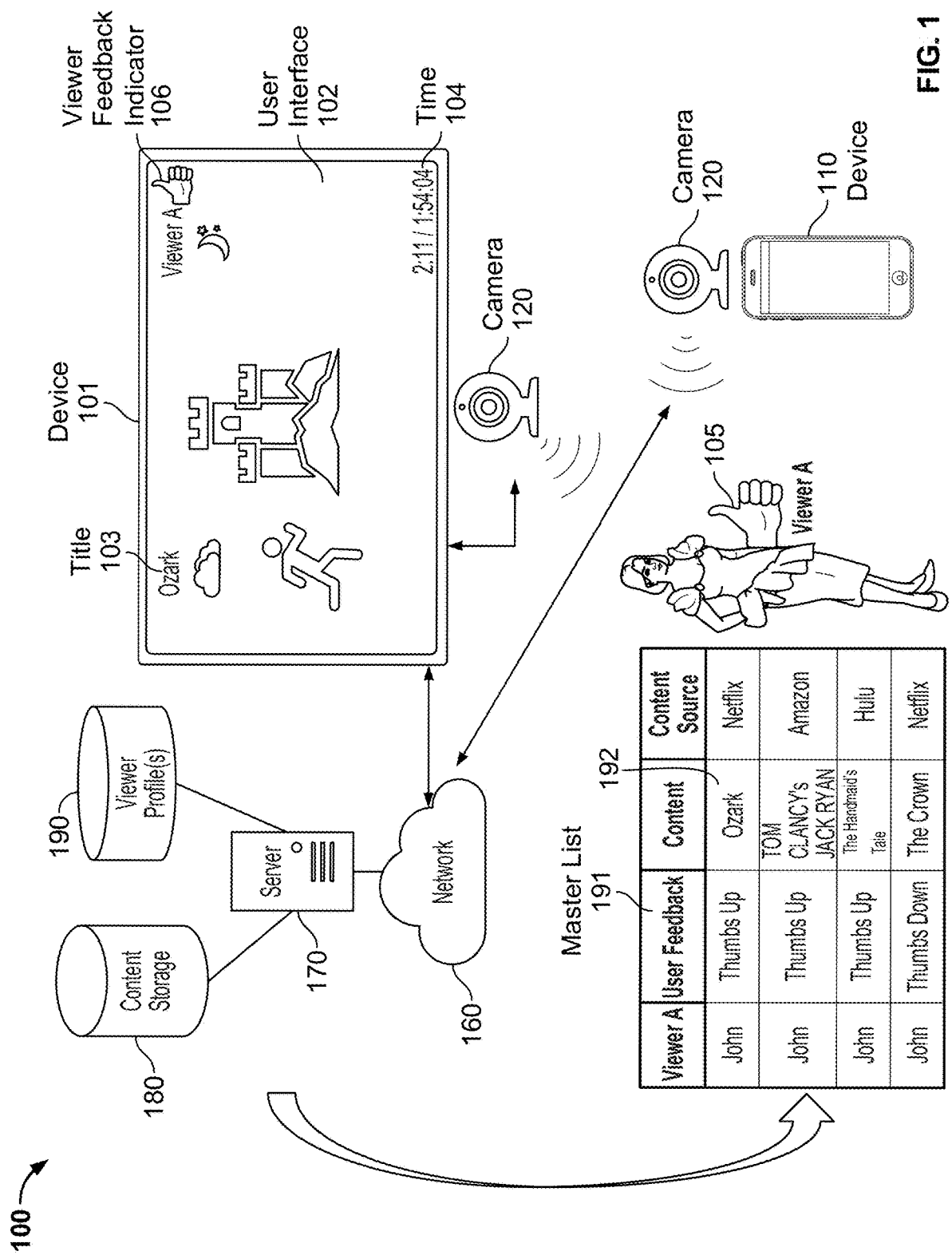
FIG. 1 shows an illustrative example of a system for providing personalized content based on captured gestures, in accordance with some embodiments of the disclosure.

FIG. 1 shows an illustrative example of a system for providing personalized content based on captured gestures, in accordance with some embodiments of the disclosure. Scenario 100 of FIG. 1 illustrates a content delivery system accessible by device 101 via network 160. In scenario 100, device 101 is illustrated as a smart television and mobile device 110 is illustrated as a smartphone. By way of a non-limiting example, scenario 100 may depict a system for capturing gestures of a user while content is generated for output on a display and utilizing the captured gestures to generate a database of a consumer's preferences as well deep links to access the content or related content.

Figure 4:
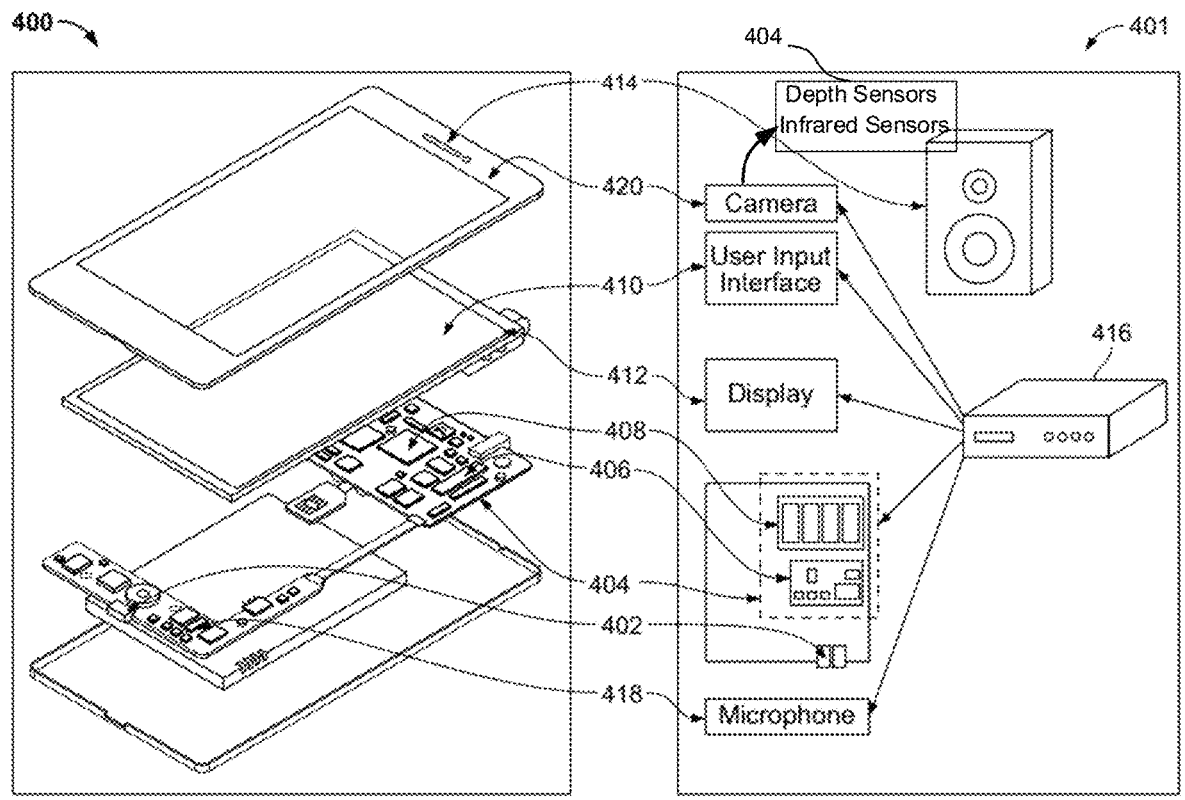
FIG. 4 depicts exemplary devices and related hardware for providing personalized content based on captured gestures, in accordance with some embodiments of the disclosure.
Figure 5:
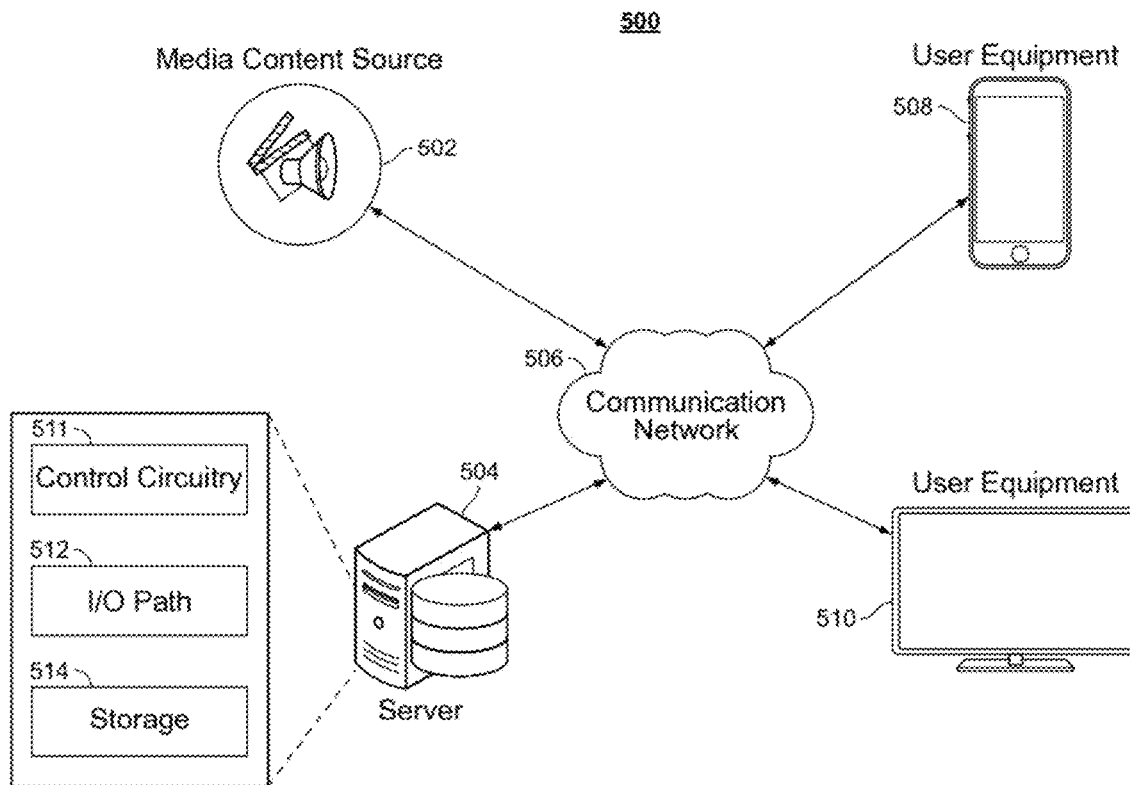
FIG. 5 depicts exemplary systems, servers and related hardware for providing personalized content based on captured gestures, in accordance with some embodiments of the disclosure.

Each of the depicted devices 101 and 110 may be any suitable device such as a television, personal computer, laptop, smartphone, tablet, media center, video console, or any device as depicted in FIGS. 4 and 5. Device 101 should have the capabilities to receive input, communicate with a network, and provide content for consumption. Input for device 101 may be from any suitable input interface such as a depth camera, touchscreen, touchpad, or stylus and/or may be responsive to external device add-ons, such as a remote control, mouse, trackball, keypad, keyboard, joystick, voice recognition interface, or other user input interfaces. The display on device 101 may be provided as a stand-alone device or integrated with other elements of each one of device 101 and system 101. For example, display 101 may be a touchscreen or touch-sensitive display. The display on device 101 may be one or more of a monitor, a television, a liquid-crystal display (LCD) for a mobile device, amorphous silicon display, low-temperature poly silicon display, electronic ink display, electrophoretic display, active matrix display, electro-wetting display, electro fluidic display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, The display on device 101 may be HDTV-capable. In some embodiments, The display on device 101 may be a 3D display, and the interactive application and any suitable content may be displayed in 3D. A video card or graphics card may generate the output to the display 101. The video card may offer various functions such as accelerated rendering of 3D scenes and 2D graphics, MPEG-2/MPEG-4 decoding, TV output, or the ability to connect multiple monitors. The video card may be any processing circuitry described below in relation to control circuitry 404. The video card may be integrated with control circuitry 404. In some embodiments, the audio may be distributed to a receiver (not shown), which processes and outputs the audio via speakers.

A capture module may be provided as integrated with the other elements of each one of device 101 and system 100 or may be a stand-alone unit. The capture module or capture engine includes a color camera and a depth camera and is configured to capture one or more images of the plurality of candidate areas. Some embodiments may utilize a capture engine, e.g., as part of an interactive content guidance application, stored and executed by one or more of the memory and processors of device 101 to capture user biometric data while a first content item is generated for presentation. Mobile device 110 is shown as an exemplary device by which the system may detect a viewer's presence and capture feedback from the viewer. Other devices and methods may be used to capture user feedback of a viewer, including the viewer logging in to a user account and to provide feedback by way of a stored visual cue, for example, a thumbs-up, or thumbs-down, or another visual cue. Mobile device 110 may be any device capable of communicating with device 101 as to the identity and relative proximity of a viewer. Mobile device 110 may be, for instance, a smartphone, tablet, watch, remote control, keyboard, smartcard, etc., having a capability to capture users' biometric data.

Interactive content guidance applications may take various forms, such as interactive television program guides, electronic program guides (EPG) and/or user interfaces, which may allow users to navigate among and locate many types of content including conventional television programming (provided via broadcast, cable, fiber optics, satellite, internet (IPTV), over-the-top (OTT) media service or other modes) and recorded programs (e.g., DVRs) as well as pay-per-view programs, on-demand programs (e.g., video-on-demand systems), internet content (e.g., streaming media, downloadable content, webcasts, shared social media content, etc.), music, audiobooks, websites, animations, podcasts, (video) blogs, ebooks, and/or other types of media and content. Such television program guides may be generated based on the user providing gesture feedback to add such content to the guide. For example, an advertisement for a second content item, e.g., "The Handmaid's Tale," may be presented for display, identifying the content source (e.g., Hulu). The consumer may further provide feedback by way of a hand gesture (e.g., thumbs-up), and in response, an indicator for the second content item, e.g., "The Handmaid's Tale," may be added to the guide for quick selection and generation for display.

The interactive guidance application guide provided may be for content available through a particular content source, for example, a television, or through one or more devices, or it may bring together content available both through a television and through internet-connected devices using interactive guidance. The content guidance applications may be provided as online applications (e.g., provided on a website), or as stand-alone applications or clients on handheld computers, mobile telephones, or other mobile devices. Various devices and platforms that may implement content guidance applications are described in more detail below.

As shown in scenario 100, device 101 generates a graphical user interface, e.g., user interface 102. In scenario 100, user interface 102 displays content delivered via network 160 by server 170 from, e.g., content storage 180. User interface 102 may display a first content item 103 (e.g., an advertisement for content or product), for example, the program "Ozark," which is exclusively offered via a Netflix subscription. During the presentation, the user may provide user's feedback 105, in the form of a hand gesture (e.g., thumbs-up, or thumbs-down, or any other feedback), or facial expression (e.g., smile, or any other feedback), or a combination thereof, or any other form of providing visual indications of users feedback. The capture engine 120 connected to device 101 or mobile device 110 may capture users' motions including hand gestures and identify a feedback indicator 105 for the viewer. In some embodiments, the captured engine 120 may be incorporated into device 101 or mobile device 110. The system may employ one or more sensors selected from depth camera sensors integrating infrared sensors, time-of-flight sensors or another camera sensors 120 or a combination of the sensors for depth sensing. Any one or more sensors from the captured engine 120, (e.g., depth camera sensors, infrared sensors, time-of-flight sensors) may capture data from the environment indicative of the depth of the object to create a three dimensional model of an object (e.g., a face, thumbs-up, etc.) within a scene from a viewpoint (e.g., a depth camera sensor). The captured data from the one or more sensors may be a visible light image, an infrared image, or a depth image. The captured data may be used to determine a depth map of different portions of an image captured that may be processed to identify the user's feedback indicator 105. In some embodiments, in response to capturing the feedback indicator 105, the user interface 102 may list the captured feedback indicator 106 on the device 101, indicating that the user likes the content item.

In some embodiments, the captured engine 120 includes image sensors 404 (e.g., one or more depth camera sensors, infrared sensors, time-of-flight sensors, etc.) that capture three-dimensional scene data that includes at least a hand 105 of a consumer. The image sensors 404 capture the biometric data (e.g., hand images) with sufficient resolution to enable the fingers and their respective positions to be distinguished. In some embodiments, the image sensors 404 also capture 2D color video images of the hand 105 and other elements of the scene. In some embodiments, the image sensors 404 are used in conjunction with other image sensors to capture the biometric data of the scene 100.

In some embodiments, the interactive guidance application guide stored based on the user's feedback indicator 106 may include an identifier of the second content item and the content source. The interactive guidance application guide may access a viewer profile in the viewer profile database 190. Viewer profile database 190 may be an aggregator and/or retriever of multiple content delivery services. For instance, viewer profile database 190 may be able to access, download, and update viewer profiles via corresponding application programming interfaces (APIs) for each service. In some embodiments, viewer profile database 190 may have usernames and passwords stored for each individual. In some embodiments, the viewer profile database 190 may have access limited to requesting profiles and enhanced content as needed, e.g., as a privacy concern.

In scenario 100, device 101 discovers the identity of the consumer via consumer detection signal 120 or another way to identify the consumer. In some embodiments, such as scenario 100, device 101 may emit a consumer detection signal to determine if any consumers (e.g., consumer devices) are within range. In some embodiments, a capture engine may infer that a particular consumer is consuming content via device 101 based on the proximity of mobile device 110, which the consumer has on his person e.g., as determined via camera 120. Consumer detection signal may be bidirectional. In some embodiments, consumer detection signals may be one or more networks using Bluetooth, near-field communication (NFC), radiofrequency, IEEE 802.11x (Wi-Fi), or other protocol(s). For instance, mobile device 110 may be a smartphone or NFC smartcard that relays an encoded consumer account. In some embodiments, a consumer detection signal may create a local area network and/or an ad-hoc network with mobile device 110. In some embodiments, consumer detection signal may use pre-established Wi-Fi to communicate. In some embodiments, consumer detection signal may connect to a common server by, e.g., accessing an activation website communicated by on-screen information, text message, QR codes, infrared, audio, or other communication. In some embodiments, a consumer may use a keypad and log in to a consumer account, e.g., via infrared remote.

In scenario 100, device 101 discovers the identity of a consumer via consumer detection signal. In some embodiments, mobile device 110 may respond to consumer detection signal from device 101 to acknowledge that a guest device is within range. For instance, device 101 and mobile device 110 may perform a handshake and/or communicate via viewer detection signal. A handshake may be used to exchange information to establish a communication protocol prior to full communication. In some embodiments, once within range, the capture engine 120 may be one of many approaches to detecting the biometric data of a consumer during consumption of the first content item. In such embodiments, privacy may be a concern, e.g., with subscription usernames and/or billing information, and data may be shared under pseudonyms or encrypted identifications. Device 101 and mobile device 110 may also communicate through a remote network, e.g., network 160.

For instance, by way of a non-limiting example, a consumer may consume content, such as a movie, a sporting event, or a news report, on a television, e.g., device 101. In such an example, device 101 may send a viewer detection signal to detect if any mobile devices are around, which may indicate that a particular consumer is viewing the playback on device 101 assuming the consumer is carrying the mobile device. If a mobile device, e.g., mobile device 110, responds, device 101 may communicate with server 170 to capture user feedback 105 for the respective consumer, e.g., "VIEWER A" with viewer feedback indicator 106 as "Thumbs-up." A feedback indicator is determined after parsing through all the images captured by the depth camera based on a particular consumer's lookup table and the preferences associated with the specific consumer. For example, a particular consumer may prefer one actor or genre or any other ascertainable variable. In some embodiments, the system identifies, based on a mapping logic from the lookup table, a media asset consumption profile for "VIEWER A" and stores, in the interactive guidance application guide (e.g., master list) 191, captured indicators 192 of the second content item (e.g., "Ozark") that the user provided a thumbs-up. The mapping logic may include for each consumer a list of content items, metadata associated with content items, indicators associated with the content items, and content sources.

Scenario 100 displays on device 101 a first content item 103. In some embodiments, in response to identifying that the feedback indicator 105 is positive during the output for consumption of the first content item 103, the system stores in a master list 191 the identifier 192 of the second content item. From the master list 191, which may be displayed on device 101 or 110 as an interactive guidance application guide or embedded within an application running on device 101 or 110, the user may select the identifier of the second content item to launch the program for presentation. Thereby the system provides to the consumer a seamless and quick launch of the second content item on the user device. Such presentation may be personalized to the user device that is employed for presentation. For example, even though the user feedback was provided on a first device, when the user selects the identifier for the second content item on a second device, the content is presented based on the second device's capabilities. In some embodiments, the user device generates for output on a display the master list. In some embodiments, responsive to a selection of the identifier of the second content item from the master list, the user device retrieves for output the second content item from the second content source on the user device.

Figure 2:
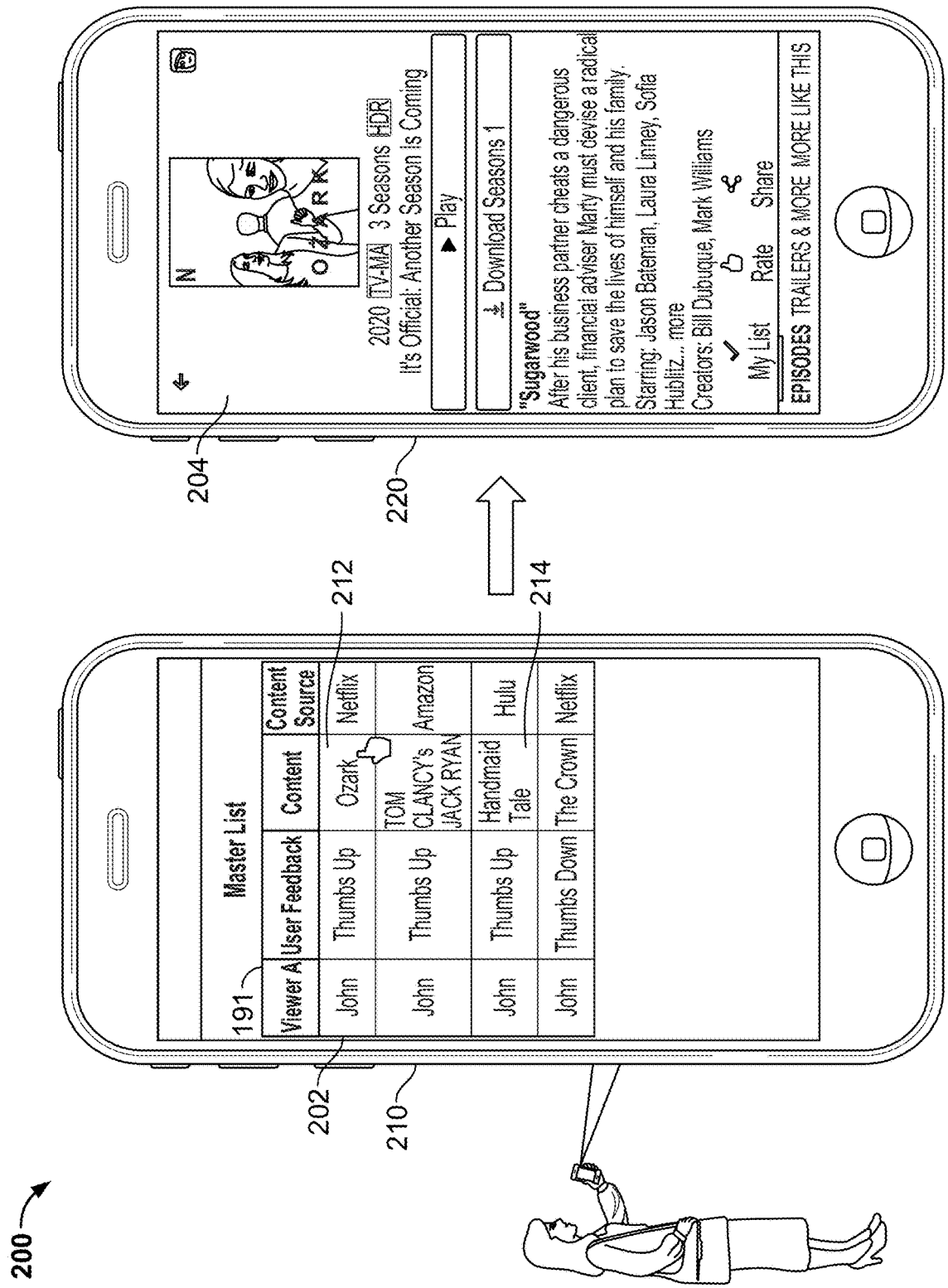
FIG. 2 shows an illustrative example of a system for providing personalized content based on captured gestures from a master list, in accordance with some embodiments of the disclosure.

FIG. 2 shows an illustrative example of a system 200 for providing personalized content based on captured gestures from a master list, in accordance with some embodiments of the disclosure. System 200, in various embodiments, may correspond to a continuation of the system of FIG. 1. Once the master list 202 is generated, control circuitry 404 accesses, via a user device 210, the master list 202. In the illustrative example of FIG. 2, the user device is a mobile device; however, such device is non-limiting and may be any device with access to the master list 202. While on the user device 210, the user may access the master list 191, in a table format or in the interactive guidance application guide, which includes captured user feedback, and select the indicator 212 for the second content item (e.g., "Ozark"). For example, an interactive guidance application guide that includes all entries captured based on user feedback, including content, user feedback and content source, may receive a selection of the indicator 212 for second content item (e.g., "Ozark"). In response to selecting indicator 212 for the second content item (e.g., "Ozark"), the user device may launch the content source (e.g., Netflix). In some embodiments, selecting indicator 212 for the second content item (e.g., "Ozark") may automatically launch the second content item for output. In another embodiment, selecting the indicator 212 for second content item (e.g., "Ozark") may prompt the content item to prompt for launch. The selection may be provided by a user accessing the master list and may be provided in any form including a voice command, selection using a mouse, touching the touch screen or any other suitable method to select the content indicator. In some embodiments, responsive to the received selection, the control circuitry launches the second content source and the content item on the user device. In some embodiments, the device makes an API call to retrieve the security data to access the content source (e.g., YouTube, Netflix, and Hulu). In some embodiments, the control circuitry may provide an alert or a notification. For example, a notification may appear on the display "You recently liked 'Ozark,' Do you want to watch it now?"). In some embodiments, selecting the indicator 214 for the content item (e.g., "The Handmaid's Tale") may automatically launch the second content source, Hulu.

Figure 3:
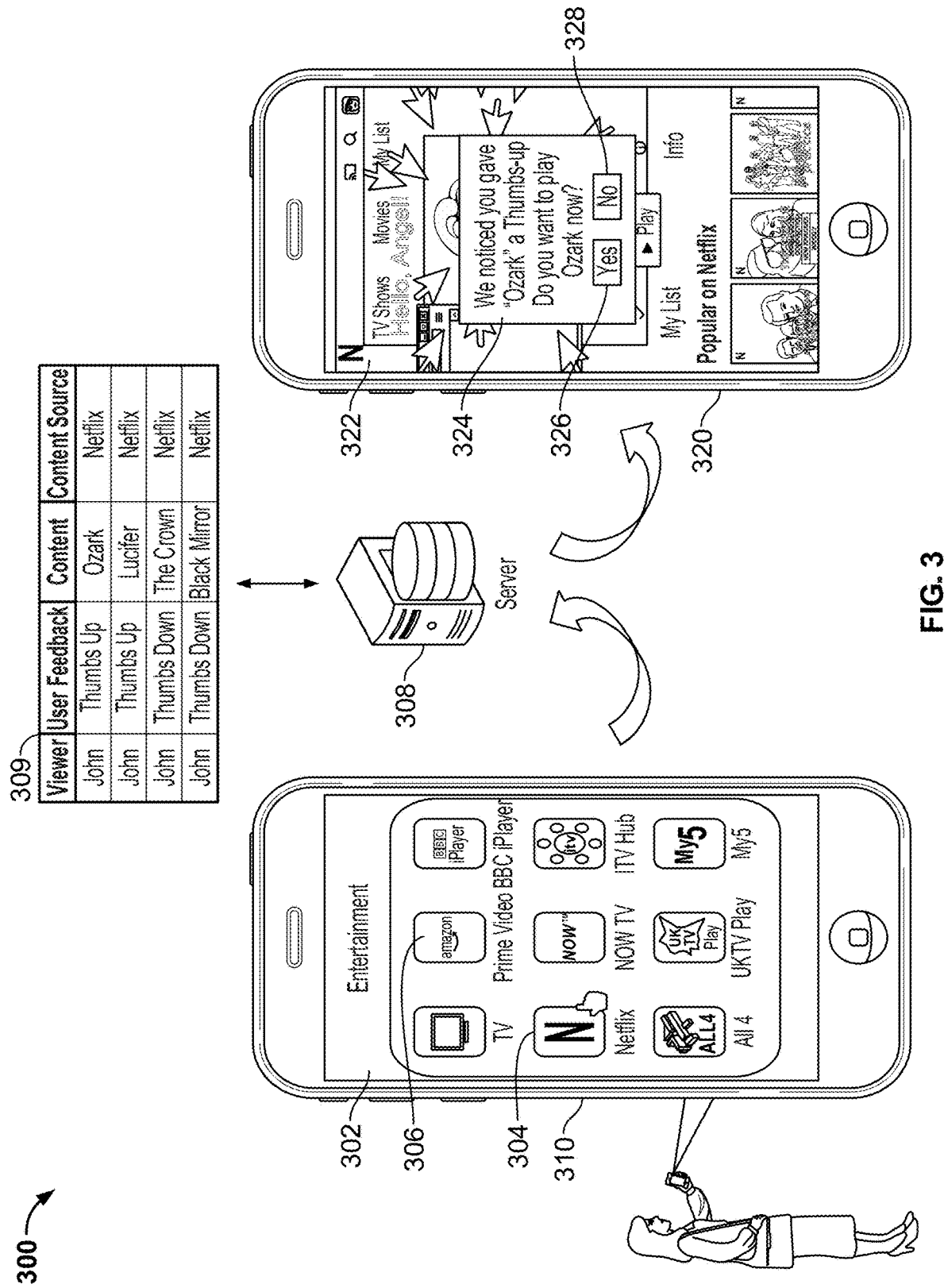
FIG. 3 depicts an illustrative example of a system for providing personalized content based on captured gestures from a third-party application on the user device, in accordance with some embodiments of the disclosure.

FIG. 3 depicts an illustrative example of a system 300 for providing personalized content based on captured gestures from a content source on the user device, in accordance with some embodiments of the disclosure. System 300, in various embodiments, may correspond to a continuation of the system of FIG. 1. Once the master list 309 is generated, control circuitry 404 accesses, via a user device 310, the master list 309. In the illustrative example of FIG. 3, the user device is a mobile device; however, such device is non-limiting and may be any device with access to the master list 309. While on the user device 310, the user may access the second content source, for example, Netflix 304, Amazon Prime Video 306. In response to accessing the content source, e.g., selecting Netflix 304, the control circuitry for the user device 310 may launch the Netflix application and simultaneously look up from a server 308 the master list 309 to determine if any content items may be generated from the second content source. In response to identifying content on the master list 309 and also provided on the second content source 304, the user device 320 may generate an alert or notification to generate for output the content item. For example, selecting Netflix may launch the Netflix application and prompt the user device 320 to provide a notice 324 to play "Ozark." The notice 324 may provide the following message "We noticed you gave 'Ozark' a thumbs-up., Do you want to play 'Ozark' now?" with the option "Yes" 326 and option "No" 328. By selecting the option "Yes" 326 from notice 324, the application will launch the content for presentation. By selecting the option "No" 328 from notice 324, the application will return to the main menu of the content source 322. In some embodiments, responsive to the received selection, the control circuitry launches the content source and the content item on the user device. In some embodiments, the device makes an API call to retrieve the security data to access the content source (e.g., YouTube, Netflix, and Hulu) when such security authentication is necessary.

FIG. 4 depicts exemplary devices and related hardware for providing personalized content based on captured gestures, in accordance with some embodiments of the disclosure. FIG. 4 shows generalized embodiments of illustrative user equipment devices 400 and 401. For example, user device 400 may be a smartphone device. In another example, user system 401 may be a user television equipment system (e.g., the computing device 506). In yet another example, the user equipment system 401 may be a media device. The user television equipment system 401 may include a set-top box 416. The set-top box 416 may be communicatively connected to a camera 420, a microphone 418, a speaker 414, and a display 412. In some embodiments, the camera 420 may detect users in the media presentation environment (i.e., the proximity of the media device) and may capture user gestures. In some embodiments, the camera 420 is a depth camera that is configured to generate a depth map that may be used to identify user feedback, for example, thumb up, thumb down, a heart, or any other gesture. In some embodiments, the microphone 418 may detect sound (e.g., background noise) in the media presentation environment. In some embodiments, the display 412 may be a television display or a computer display (i.e., the proximity of the media device). In some embodiments, the set-top box 416 may be communicatively connected to a user input interface 410. In some embodiments, the user input interface 410 may be a remote-control device (e.g., the remote control). The set-top box 416 may include one or more circuit boards. In some embodiments, the circuit boards may include processing circuitry, control circuitry, and storage (e.g., RAM, ROM, hard disk, removable disk, etc.). In some embodiments, the circuit boards may include an input/output path. More specific implementations of user devices are discussed below in connection with FIG. 5. Each one of the user device 400 and the user equipment system 401 may receive content and data via input/output (I/O) path 402. The I/O path 402 may provide content (e.g., broadcast programming, on-demand programming, internet content, content available over a local area network (LAN) or wide area network (WAN), and/or other content) and data to control circuitry 404, which includes processing circuitry 406 and a storage 408. The control circuitry 404 may be used to send and receive commands, requests, and other suitable data using the I/O path 402. The I/O path 402 may connect the control circuitry 404 (and specifically the processing circuitry 406) to one or more communications paths (described below). I/O functions may be provided by one or more of these communications paths, but are shown as a single path in FIG. 4 to avoid overcomplicating the drawing.

The control circuitry 404 may be based on any suitable processing circuitry, such as the processing circuitry 406. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, the control circuitry 404 executes instructions for a media device stored in memory (i.e., the storage 408). Specifically, the control circuitry 404 may be instructed by the media device to perform the functions discussed above and below including capturing user feedback and using the feedback to generate a database that is easily accessible. In some implementations, any action performed by the control circuitry 404 may be based on instructions received from the media device.

In client/server-based embodiments, the control circuitry 404 may include communications circuitry suitable for communicating with a media device server or other networks or servers. The instructions for carrying out the above-mentioned functionality may be stored on a server (which is described in more detail in connection with FIG. 5). Communications circuitry may include a cable modem, an integrated services digital network (ISDN) modem, a digital subscriber line (DSL) modem, a telephone modem, an Ethernet card, or a wireless modem for communications with other equipment, or any other suitable communications circuitry. Such communications may involve the internet or any other suitable communication networks or paths (which is described in more detail in connection with FIG. 5). In addition, communications circuitry may include circuitry that enables peer-to-peer communication of user devices, or communication of user equipment devices in locations remote from each other (described in more detail below).

Memory may be an electronic storage device provided as the storage 408 that is part of the control circuitry 404. As referred to herein, the phrase "electronic storage device" or "storage device" should be understood to mean any device for storing electronic data, computer software, or firmware, such as random-access memory, read-only memory, hard drives, optical drives, digital video recorders (DVRs, sometimes called personal video recorders, or PVRs), solid state devices, quantum storage devices, gaming consoles, gaming media, or any other suitable fixed or removable storage devices, and/or any combination of the same. The storage 408 may be used to store various types of content described herein as well as media device data described above. For example, the storage 408 may be used to store the output volume adjustment profiles described in FIG. 2. Nonvolatile memory may also be used (e.g., to launch a boot-up routine and other instructions). Cloud-based storage, described in relation to FIG. 5, may be used to supplement the storage 408 or instead of the storage 408.

The control circuitry 404 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. The control circuitry 404 may also include scaler circuitry for upconverting and downconverting content into the preferred output format of the user equipment 400. The circuitry 404 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general-purpose or specialized processors. Multiple tuners may be provided to handle simultaneous tuning functions (e.g., watch and record functions, picture-in-picture (PIP) functions, multiple-tuner recording, etc.). If the storage 408 is provided as a separate device from the user equipment device 400, the tuning and encoding circuitry (including multiple tuners) may be associated with the storage 408.

A user may send instructions to the control circuitry 404 using the user input interface 410. The user input interface 410 may be any suitable user interface, such as a remote control, mouse, trackball, keypad, keyboard, touchscreen, touchpad, stylus input, joystick, voice recognition interface, or other user input interfaces. The display 412 may be provided as a stand-alone device or integrated with other elements of each one of the user equipment device 400 and the user equipment system 401. For example, the display 412 may be a touchscreen or touch-sensitive display. In such circumstances, the user input interface 410 may be integrated with or combined with display 412. The display 412 may be one or more of a monitor, a television, a display for a mobile device, or any other type of display. A video card or graphics card may generate the output to the display 412. The video card may be any processing circuitry described above in relation to the control circuitry 404. The video card may be integrated with the control circuitry 404. Speakers 414 may be provided as integrated with other elements of each one of the user equipment device 400 and the user equipment system 401 or may be stand-alone units. The audio component of videos and other content displayed on the display 412 may be played through the speakers 414. In some embodiments, the audio may be distributed to a receiver (not shown), which processes and outputs the audio via speakers 414.

The media device may be implemented using any suitable architecture. For example, it may be a stand-alone application wholly implemented on each one of the user equipment device 400 and the user equipment system 401. In such an approach, instructions of the application are stored locally (e.g., in the storage 408), and data for use by the application is downloaded on a periodic basis (e.g., from an out-of-band feed, from an internet resource, or using another suitable approach). The control circuitry 404 may retrieve instructions of the application from the storage 408 and process the instructions to rearrange the segments as discussed. Based on the processed instructions, the control circuitry 404 may determine what action to perform when input is received from the user input interface 410. For example, movement of a cursor on a display up/down may be indicated by the processed instructions when the user input interface 410 indicates that an up/down button was selected.

In some embodiments, the media device is a client/server-based application. Data for use by a thick or thin client implemented on each user device 400 and the user equipment system 401 is retrieved on-demand by issuing requests to a server remote to each of the user device 400 and the user equipment system 401. In one example of a client/server-based guidance application, the control circuitry 404 runs a web browser that interprets web pages provided by a remote server. For example, the remote server may store the instructions for the application in a storage device. The remote server may process the stored instructions using circuitry (e.g., the control circuitry 404) and modify a stored relationship status based on a relationship and user feedback and automatically perform actions that control the playing of the content as discussed. In some embodiments, the remote server may process the stored instructions using circuitry (e.g., the control circuitry 404) based a change in the number of users in the proximity of the media device. For example, a second user entering the proximity and similarly leaving the proximity.

In some embodiments, the media device is downloaded and interpreted or otherwise run by an interpreter or virtual machine (run by the control circuitry 404). In some embodiments, the media device may be encoded in the ETV Binary Interchange Format (EBIF), received by the control circuitry 404 as part of a suitable feed, and interpreted by a user agent running on the control circuitry 404. For example, the media device may be an EBIF application. In some embodiments, the media device may be defined by a series of JAVA-based files that are received and run by a local virtual machine or other suitable middleware executed by control circuitry 404. In some of such embodiments (e.g., those employing MPEG-2 or other digital media encoding schemes), the media device may be, for example, encoded and transmitted in an MPEG-2 object carousel with the MPEG audio and video packets of a program.

Content and/or data delivered to user device 400 and the user equipment system 401 may be over-the-top (OTT) content. OTT content delivery allows internet-enabled user devices, such as user device 400 and the user equipment system 401, to receive content that is transferred over the internet, including any content described above, in addition to content received over cable or satellite connections. OTT content is delivered via an internet connection provided by an internet service provider (ISP), but a third party distributes the content. The ISP may not be responsible for the viewing abilities, copyrights, or redistribution of the content, and may transfer only IP packets provided by the OTT content provider. Examples of OTT content sources include YOUTUBE, NETFLIX, and HULU, which provide audio and video via IP packets. YouTube is a trademark owned by Google LLC; Netflix is a trademark owned by Netflix, Inc.; and Hulu is a trademark owned by Hulu, LLC. OTT content source may additionally or alternatively provide media guidance data described above. In addition to content and/or media guidance data, providers of OTT content, also referred to as "content source," can distribute applications (e.g., web-based applications or cloud-based applications), or the content can be displayed by applications stored on user device 400 and the user equipment system 401.

FIG. 5 depicts exemplary systems, servers and related hardware for providing personalized content based on captured gestures, in accordance with some embodiments of the disclosure. User equipment devices 508 and 510 (such as the user device 400 and the user equipment system 401) may be coupled to communication network 506. The communication network 506 may be one or more networks including the internet, a mobile phone network, mobile voice or data network (e.g., a 4G or LTE network), cable network, public switched telephone network, or other types of communications network or combinations of communication networks. Paths (e.g., depicted as arrows connecting the respective devices to the communication network 506) may separately or together include one or more communications paths, such as a satellite path, a fiber-optic path, a cable path, a path that supports internet communications (e.g., IPTV), free-space connections (e.g., for broadcast or other wireless signals), or any other suitable wired or wireless communications path or combination of such paths. Communications with the client devices may be provided by one or more of these communications paths but are shown as a single path in FIG. 5 to avoid overcomplicating the drawing.

Although communications paths are not drawn between user equipment devices, these devices may communicate directly with each other via communications paths such as short-range communication paths, point-to-point communications paths, such as USB cables, IEEE 1394 cables, wireless paths (e.g., Bluetooth, infrared, IEEE 802-11x, etc.), or other short-range communication via wired or wireless paths. The user equipment devices may also communicate with each other directly through an indirect path via the communication network 506.

The system 500 includes a media content source 502 and a server 504. Communications with the media content source 502 and the server 504 may be exchanged over one or more communications paths but are shown as a single path in FIG. 5 to avoid overcomplicating the drawing. In addition, there may be more than one of each of the media content source 502 and the server 504, but only one of each is shown in FIG. 5 to avoid overcomplicating the drawing. If desired, the media content source 502 and the server 504 may be integrated as one source device.

In some embodiments, the server 504 may include control circuitry 511 and a storage 514 (e.g., RAM, ROM, hard disk, removable disk, etc.). The server 504 may also include an input/output path 512. The I/O path 512 may provide device information, or other data, over a local area network (LAN) or wide area network (WAN), and/or other content and data to the control circuitry 511, which includes processing circuitry, and the storage 514. The control circuitry 511 may be used to send and receive commands, requests, and other suitable data using the I/O path 512. The I/O path 512 may connect the control circuitry 511 (and specifically processing circuitry) to one or more communications paths.

The control circuitry 511 may be based on any suitable processing circuitry such as one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, control circuitry 511 may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, the control circuitry 511 executes instructions for an emulation system application stored in memory (e.g., the storage 514). Memory may be an electronic storage device provided as the storage 514 that is part of the control circuitry 511.

The server 504 may retrieve guidance data from media content source 502, process the data as will be described in detail below, and forward the data to the user equipment devices 508 and 510. The media content source 502 may include one or more types of content distribution equipment including an audio distribution facility, a television distribution facility, cable system headend, satellite distribution facility, programming sources (e.g., television broadcasters, such as NBC, ABC, HBO, etc.), intermediate distribution facilities and/or servers, internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Media content source 502 may be the originator of content (e.g., a television broadcaster, a Webcast provider, etc.) or may not be the originator of content (e.g., an on-demand content provider, an internet provider of content of broadcast programs for downloading, etc.). The media content source 502 may include cable sources, satellite providers, on-demand providers, internet providers, over-the-top content providers, or other providers of content. The media content source 502 may also include a remote media server used to store different types of content (including video content selected by a user) in a location remote from any of the client devices.

Client devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices (such as, e.g., server 504), which may be located centrally or at distributed locations, that provide cloud-based services to various types of users and devices connected via a network (such as the internet) via communication network 506. In such embodiments, user equipment devices may operate in a peer-to-peer manner without communicating with a central server.

FIGS. 6A-F depict illustrative examples of a database for providing personalized content based on captured gestures, in accordance with some embodiments of the disclosure. FIG. 6A depicts an illustrative table 602 for user feedback captured using a depth camera, in accordance with some embodiments of the disclosure. In some embodiments, user feedback 602 depicts preference data for a viewer regarding content. In some embodiments, user feedback 602 may be part of a viewer profile, which may be stored in a viewer profile database, such as viewer profile database 190 of FIG. 1. User feedback 602 may be a data structure including fields with information, for instance, Viewer, User Feedback, Content and Content Source. Each field includes information that was captured for a specific user. In the illustrative example, the information provided is for viewer John and includes his captured feedback (e.g., thumbs-up and thumbs-down), the content title (e.g., "Ozark," "Tom Clancy's Jack Ryan," "Handmaids Tale," etc.) and content source (e.g., Netflix, Amazon, a store, Spotify).

FIG. 6B depicts an illustrative table for viewer preference 610, in accordance with some embodiments of the disclosure. In some embodiments, content metadata (e.g., as depicted in FIG. 6B) may be compared to viewer preferences (e.g., as depicted in FIG. 6A) to determine recommendations, in some cases to narrow down the user feedback to specific features of the content. In some embodiments, viewer preference 610 may be associated with content, which may be stored in a database, such as content storage 180 of FIG. 1. Viewer preference 610 may be stored as part of a data structure including fields with information. For instance, Genres field 612 includes "Drama, Romance, Holiday"; Actors field 614 includes "Bradley Cooper, Hugh Grant Meryl Streep"; Settings field 616 includes "London, Paris, Ancient Egypt Beaches"; Characters field 620 includes "Strong Fem. Lead, Health Professionals, Mentors"; and Scenes Dislike 630 includes "Gun Violence, War, Spiders/Bugs."

FIG. 6C depicts an illustrative table for scene metadata, in accordance with some embodiments of the disclosure. In some embodiments, scene metadata (e.g., as depicted in FIG. 6C) may be compared to viewer preferences (e.g., as depicted in FIG. 6B) in order to determine whether a scene or segments contain information that the user has an interest in. In some embodiments, scene metadata 670 may be associated with content, which may be stored in a database, such as content storage 180 of FIG. 1. Scene metadata 670 may be stored as part of a data structure including fields with information. For instance, Scene field 671 includes "034"; Genres field 672 includes "Action, Superhero"; Actors field 674 includes "John Krasinski"; Settings field 676 includes "Spaceship, Space"; Characters field 678 includes "Superheroes, Sidekicks"; and Tags field 679 includes "Friendship, Space Battle."

FIG. 6D depicts an illustrative table for content metadata, in accordance with some embodiments of the disclosure. In some embodiments, content metadata 640 may be associated with content, which may be stored in a database, such as content storage 180 of FIG. 1. Content metadata 640 may be stored as part of a data structure including fields with information. For instance, Genres field 642 includes "Action, Drama, Superhero"; Actors field 644 includes "Chris Pratt, Zoe Saldana, Bradley Cooper"; Settings field 646 includes "Space, Alien Planets"; Characters field 648 includes "Superheroes, Strong Fem. Lead, Team"; and Themes field 650 includes "Teamwork, Family, Diversity."

FIG. 6E depicts an illustrative table for products that users have provided feedback for, according to some embodiments of the disclosure. In some embodiments, the user may be consuming content and provide user feedback in order to show an interest in a particular product. In some embodiments, product 680 may be associated with content, which may be stored in a database, such as content storage 180 of FIG. 1 or added to a shopping list. Product list 680 may be stored as part of a data structure including fields with information. For instance, Product Type field 681 includes headphones, and Label includes "Boss Noise-Cancelling QC35."

FIG. 6F depicts an illustrative table for audio, in accordance with some embodiments of the disclosure. In some embodiments, the user may be consuming audio content and provide user feedback in order to determine the information that the user has an interest in. In some embodiments, audio 690 may be associated with content, which may be stored in a database, such as content storage 180 of FIG. 1. Audio 690 may be stored as part of a data structure including fields with information. For instance, Label field 691 includes song titles, e.g., "Happy" See FIG. 6F, and features field includes "Pop, Top Hits."

Figure 7:
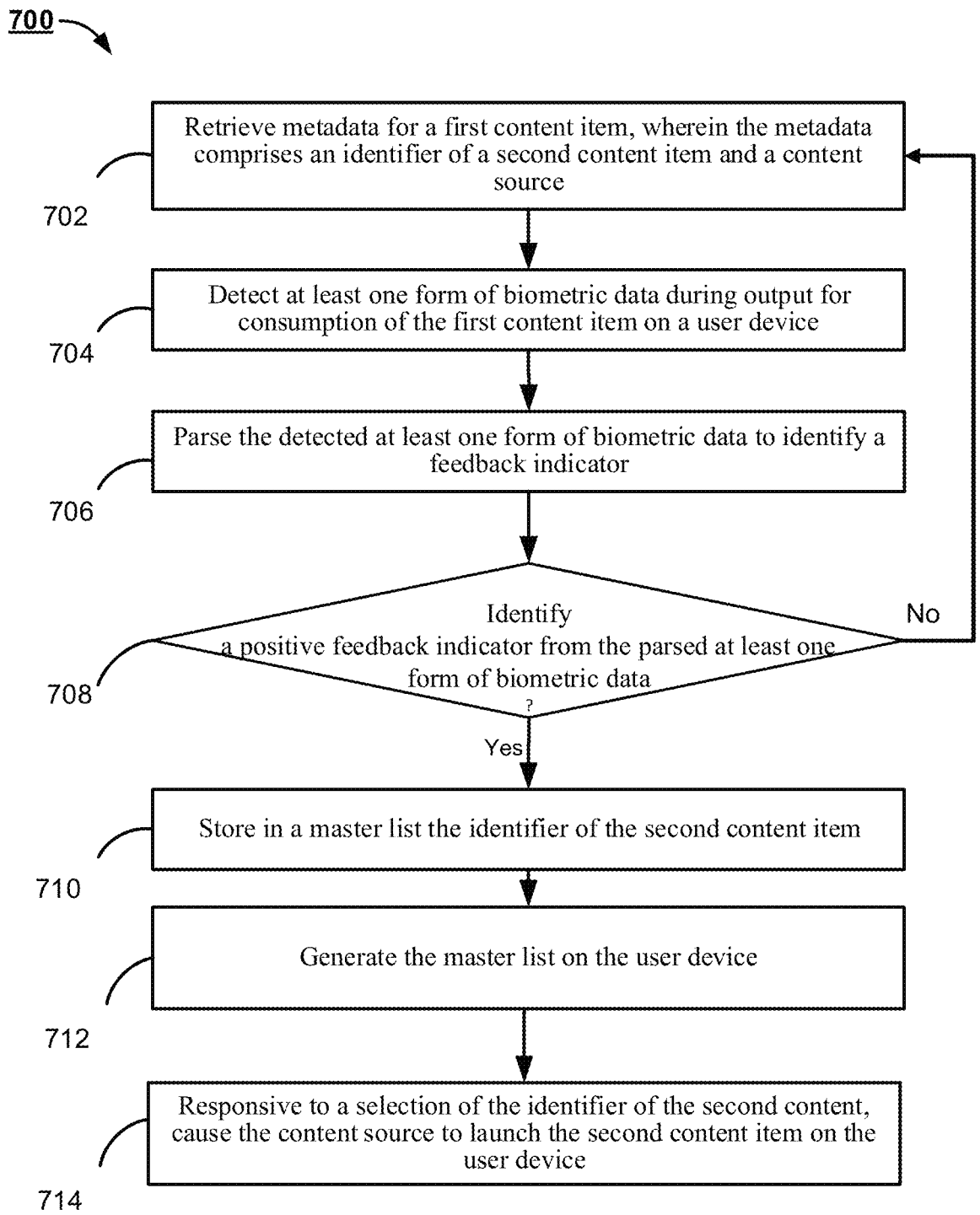
FIG. 7 is a flowchart of a detailed illustrative process for providing personalized content based on captured gestures, in accordance with some embodiments of the disclosure.

FIG. 7 is a flowchart of a detailed illustrative process for providing personalized content based on captured gestures, in accordance with some embodiments of the disclosure.

Having described system 400, reference is now made to FIG. 7, which depicts an illustrative flowchart of process 700 for providing personalized content based on captured gestures that may be implemented by using system 400, in accordance with some embodiments of the disclosure. In various embodiments, individual steps of process 700, or any process described herein, may be implemented by one or more components of system 400. Although the present disclosure may describe certain steps of process 700 (and of other processes described herein) as being implemented by certain components of system 400, this is for purposes of illustration only, and it should be understood that other components of system 400 may implement those steps instead.

At 702, control circuitry 404 retrieves metadata for a first content item, wherein the metadata comprises an identifier of a second content item and a content source. Control circuitry 404 stores the content received at storage 408. At 704, control circuitry 404 detects at least one form of biometric data during output for consumption of the first content item on a user device. Example types of biometric data that may be detected are heart rate, user gestures, and user facial expressions, as types of data that may also be included in gaming logs. In some examples, at 706, control circuitry 404 parses the detected at least one form of biometric data to identify a feedback indicator. The feedback indicators indicate whether the content being presented is liked or disliked by the user. For example, control circuitry 404 may determine whether the feedback is enabled and/or store that information in storage 408, in server database 504, or in another storage. If control circuitry does not identify a positive feedback indicator from the parsed at least one form of biometric data ("No" at 708), then procedure 700 terminates. If control circuitry does identify a positive feedback indicator from the parsed at least one form of biometric data ("Yes" at 708), then control circuitry passes to 710, at which control circuitry 404 stores the identifiers of content being presents in a master list. Additional details on how the control circuitry 404 may make the determination at 708 are provided below in connection with FIG. 8.

At 712, control circuitry 404 generates the master list for display on the user device. For example, the user accesses the master list on the user device to access the content saved on the master list. Further, in response to a selection of the identifier of the second content item, the control circuitry causes the content source to launch the second content item on the user device.

Figure 8:
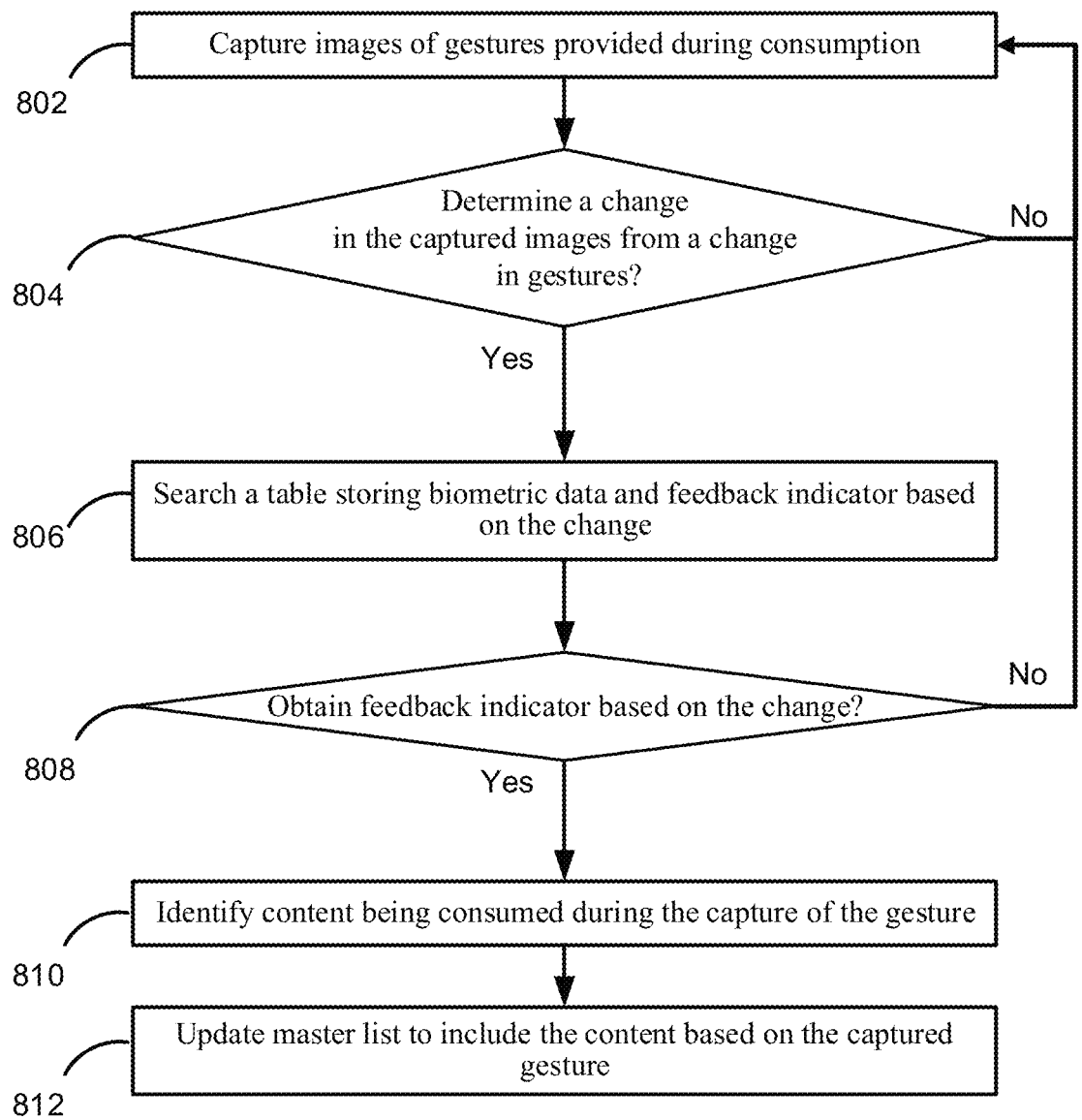
FIG. 8 is a flowchart of another detailed illustrative process for providing personalized content based on captured gestures, in accordance with some embodiments of the disclosure.

FIG. 8 is a flowchart of another detailed illustrative process 800 for providing personalized content based on captured gestures, in accordance with some embodiments of the disclosure. Process 800, in various embodiments, may correspond to steps 704-708 of FIG. 7. At 802, control circuitry 404 captures images of the user including biometric data (e.g., user gestures), during content being generated for output. For example, a depth camera may be utilized for the capture of the image to generate three-dimensional images. At 804, control circuitry 404, with the use of a depth map identified from the depth camera, determines a change in gestures based on a change in lighting in the captured images that correlate to movement of the user's limbs from storage 408. A threshold or a minimum number of changes would indicate a gesture and compare the threshold to the number of changes extracted from the captured image of biometric data at 802. If the number of changes extracted from the biometric data captured at 802 meets or exceeds the threshold ("Yes" at 804), then, at 806, control circuitry 404 searches the biometric data (e.g., captured images) and feedback templates (e.g., gesture models from storage 408) based on the change to identify a feedback indicator that indicates the user's feedback. In some embodiments, the control circuitry may compare the generated 3-dimensional image to gesture models to determine if one or more are pre-stored feedback indicators are identified. If the number of changes extracted from the biometric data captured 802 does not meet or exceed the threshold ("No" at 804), then control circuitry 404 returns to 802 to capture images. In some embodiments, continuing at 808, control circuitry 404 determines a feedback indicator based on the search of the biometric data to identify a number of changes in the hand gesture. Such identified number of changes is compared against a threshold or the minimum number of changes that would indicate a gesture, which correlate to the gesture models from storage 408. If the number of changes extracted from the biometric data captured at 802 meets or exceeds the threshold ("Yes" at 808), then, at 810, control circuitry 404 identifies the content being generated for consumption and, at 812, stores indicators of the content in the master list, including shortcut links or deep links. If the number of changes extracted from the biometric data captured 802 does not meet or exceed the threshold ("No" at 808), then, control circuitry 404 returns to 802 to capture images.

Figure 9:
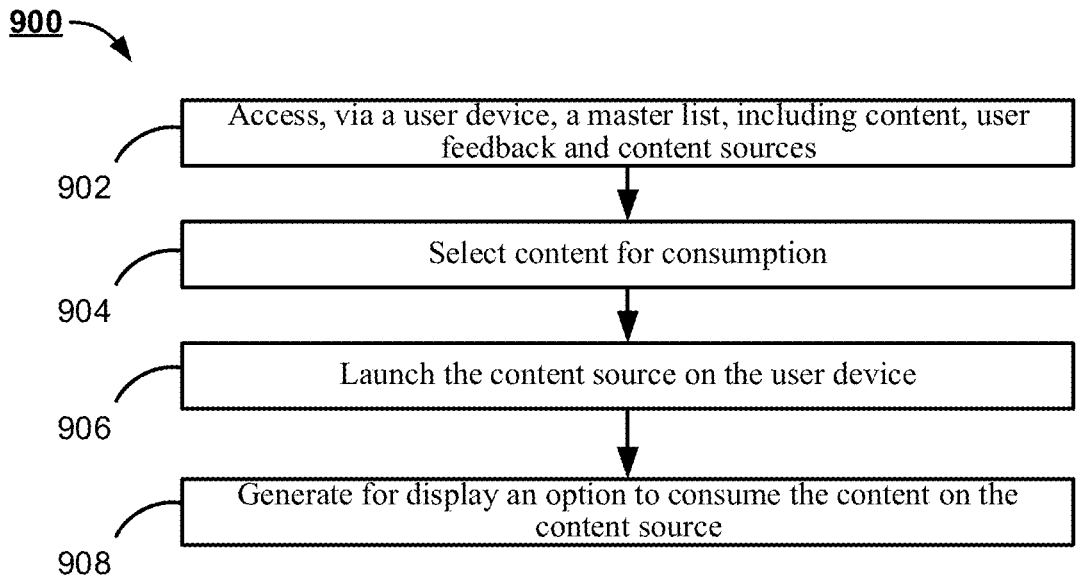
FIG. 9 is a flowchart of a detailed illustrative process for providing personalized content based on captured gestures from a master list, in accordance with some embodiments of the disclosure.

FIG. 9 is a flowchart of a detailed illustrative process 900 for providing personalized content based on captured gestures from a master list, in accordance with some embodiments of the disclosure. Process 900, in various embodiments, may correspond to step 712 of FIG. 7. At 902, control circuitry 404 accesses, via a user device, the master list, for example, an interactive guidance application guide that includes all entries captured based on user feedback, including content, user feedback and content source. At 904, control circuitry 404 receives selection of content (e.g., "Ozark") from the interactive guidance application guide. The selection may be provided by a user accessing the master list and may be provided in any form including voice command, selection using a mouse, touching the touch screen, or any other suitable method to select the content. Responsive to the received selection at 904, at 906, the control circuitry launches the content source on the user device. In some embodiments, the device makes an API call to retrieve the security data to access the content source (e.g., YouTube, Netflix, and Hulu). The process continues at 908 to generate for display an option to consume the content on the content source. For example, the control circuitry may provide an option to generate the content (e.g., "Ozark") for presentation. In some embodiments, the control circuitry may provide an alert or a notification. For example, a notification may appear on the display "You recently liked 'Ozark', do you want to watch it now?"). In another example, in response to receiving a thumbs-up to an advertisement, where the content item may be purchased for consumption, a confirmation may appear on the user device (e.g., television) "You recently liked 'Ozark.' Do you want to rent it now?"). In response to the requested confirmation, the user device may capture hand gestures from the consumer to confirm the purchase. For example, a thumbs-up may indicate to proceed with the purchase, while a thumbs-down may turn down the offer.

In some embodiments, the captured feedback may also be in response to a content item being presented. For example, when providing feedback after a movie was presented on the television. In some embodiments, the captured feedback may be employed to provide a numerical sliding rating. For example, capturing a thumbs-up, and leaving the thumps-up hand gesture, the user device (e.g., television or camera system associated with the television) may provide a rating is keep increasing based on the length of the thumbs-up. In one example, by providing a numerical rating, a quick (e.g., 1 second) thumbs-up leads to a rating of 60%. In another example, as the consumer provides a thumbs-up for 10 seconds, the rating may gradually increase to 90%. The user device may adjust the rating based on the consumer providing a thumbs-down.

Figure 10:
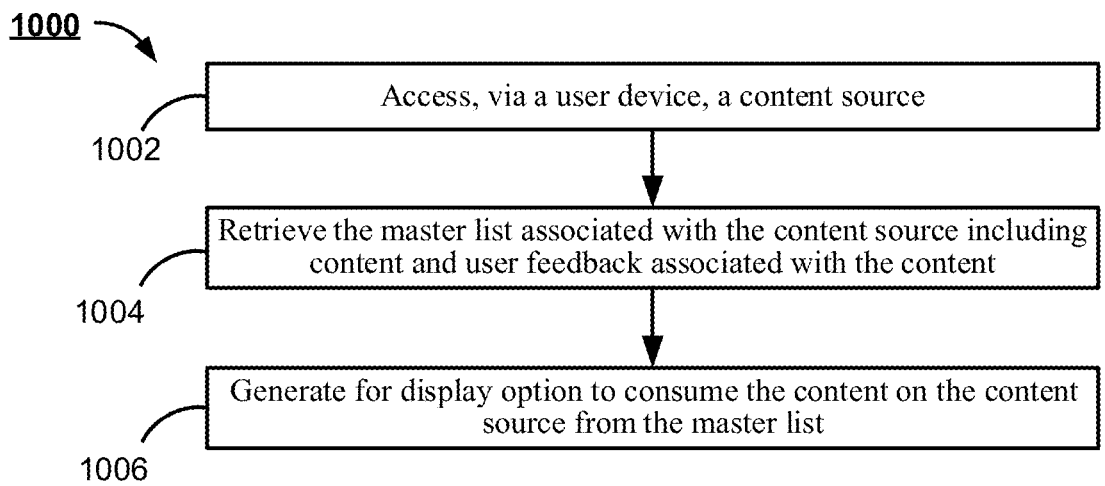
FIG. 10 is a flowchart of a detailed illustrative process for providing personalized content based on captured gestures from the third-party application, in accordance with some embodiments of the disclosure.

FIG. 10 is a flowchart of a detailed illustrative process 1000 for providing personalized content based on captured gestures from the third-party application, in accordance with some embodiments of the disclosure. Process 1000, in various embodiments, may correspond to step 712 of FIG. 7. At 1002, control circuitry 404 accesses, via a user device, the content source (e.g., YouTube, Netflix, and Hulu). At 1004, control circuitry 404 retrieves the master list associated with the content source including content and user feedback associated with the content selection (e.g., "Ozark") from the interactive guidance application guide. In response to launching, e.g., Netflix at 1002, the control circuitry filters all content on the master list and presents only content from the content source (e.g., "Netflix"). Responsive to the retrieved master list at 1004, at 1006, the control circuitry continues at 1006 to generate for display an option to consume the content on the content source. For example, the control circuitry may provide an option to generate the content (e.g., "Ozark") for presentation. In some embodiments, the control circuitry may provide an alert or a notification. For example, a notification may appear on display such as "You recently liked 'Ozark.' Do you want to watch it now?").

Figure 11:
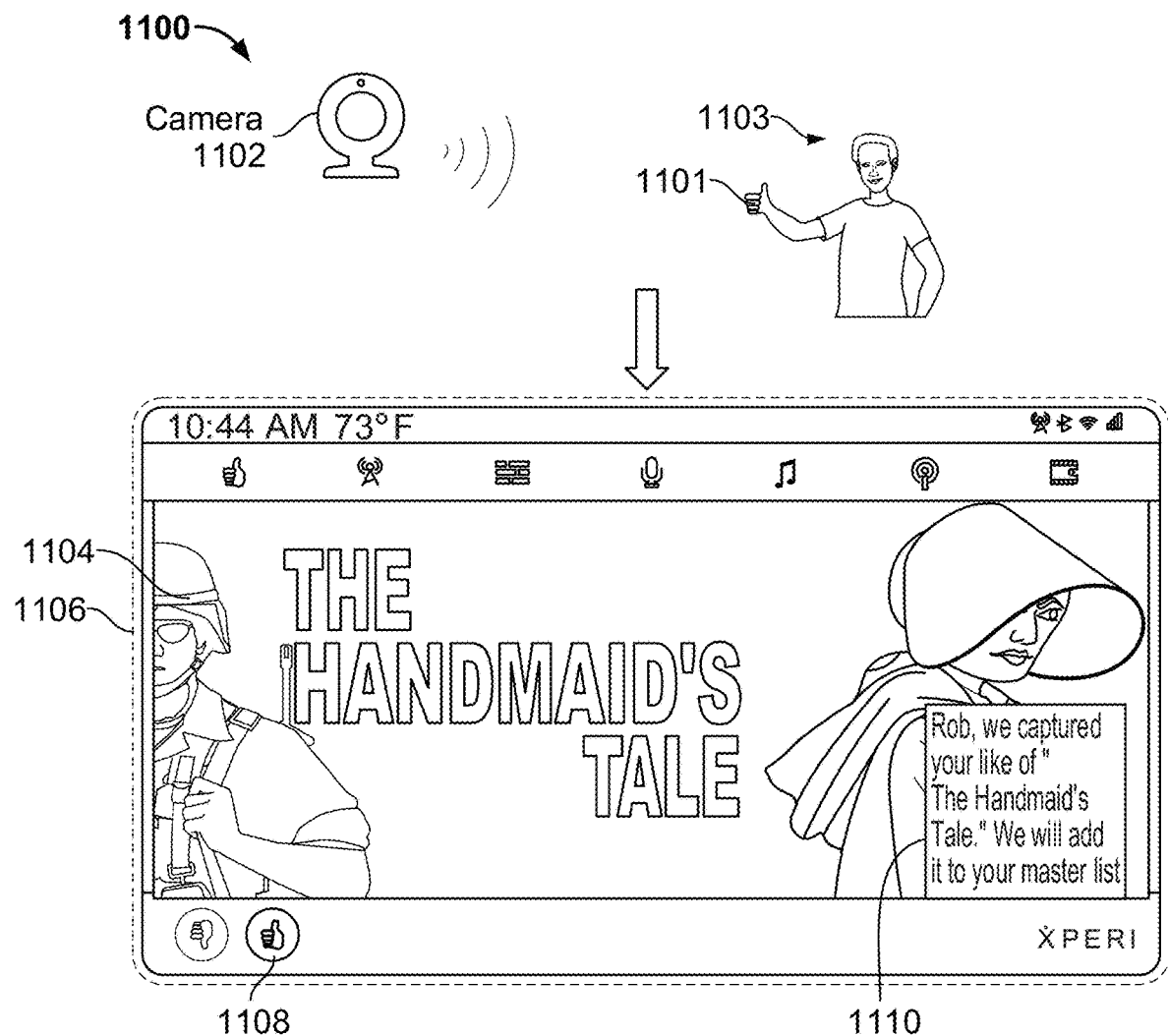
FIG. 11 is a detailed illustrative process for providing personalized content based on captured gestures displaying an interactive media guidance interface, in accordance with some embodiments of the disclosure.

FIG. 11 is a detailed illustrative process 1100 for providing personalized content based on captured gestures displaying an interactive media guidance interface, according to some embodiments of the disclosure. Process 1100 provides an illustrative example of a user providing feedback with the use of hand gestures. In some embodiments, the user 1103 may provide a hand gesture 1101 during output for the presentation of an advertisement or a content item 1104 on display 1106. For example, a thumbs-up that is captured by a first device. In some embodiments, the device (e.g., mobile phone) capturing the user gesture may be a different device than the device (e.g., television, display) outputting the content for presentation. In such an aspect of this embodiment, the devices (first device and second device) may be communicating via an internet connection, a Bluetooth connection, a Wi-Fi connection or any other suitable way for multiple devices to transfer information. In some embodiments, both devices are providing information to a centralized database stored in a server or the cloud. For example, the first device may transmit the captured feedback to a database for the user profile, which may cause the second device to receive a request to provide information on the content being output. The devices may align the captured feedback with timestamps that correlate to the time range of the content being output on the second device. In response to the captured hand gesture, the control circuitry may provide an alert or a notification 1110 on one device, for example, the display 1106. Such notification may be provided on a second device or transmitted to the user profile as a message. In some embodiments, a notification may appear on display "Rob, we captured your like of The Handmaid's Tale. We will add it to your master list." In some embodiments, the master list may be any list generated for providing quick access and retrieval of content to the user. In some embodiments, a thumbs-up or a thumbs-down icon on the interactive media guidance interface may be highlighted as an indication of capturing the user's feedback.

In some embodiments, the control circuitry of one device may capture the user's feedback during a second device (e.g., movie projector) outputting content for consumption. For example, while a user is in a movie theater and a movie preview is output for presentation, the first device (e.g., mobile device) may capture the user's biometric data indicative of the user liking or disliking the movie preview. In some embodiments, such captured biometric data that includes a thumbs-up or thumbs-down may be utilized to alert the user when the movies liked by the user are released for presentation.

Figure 12:
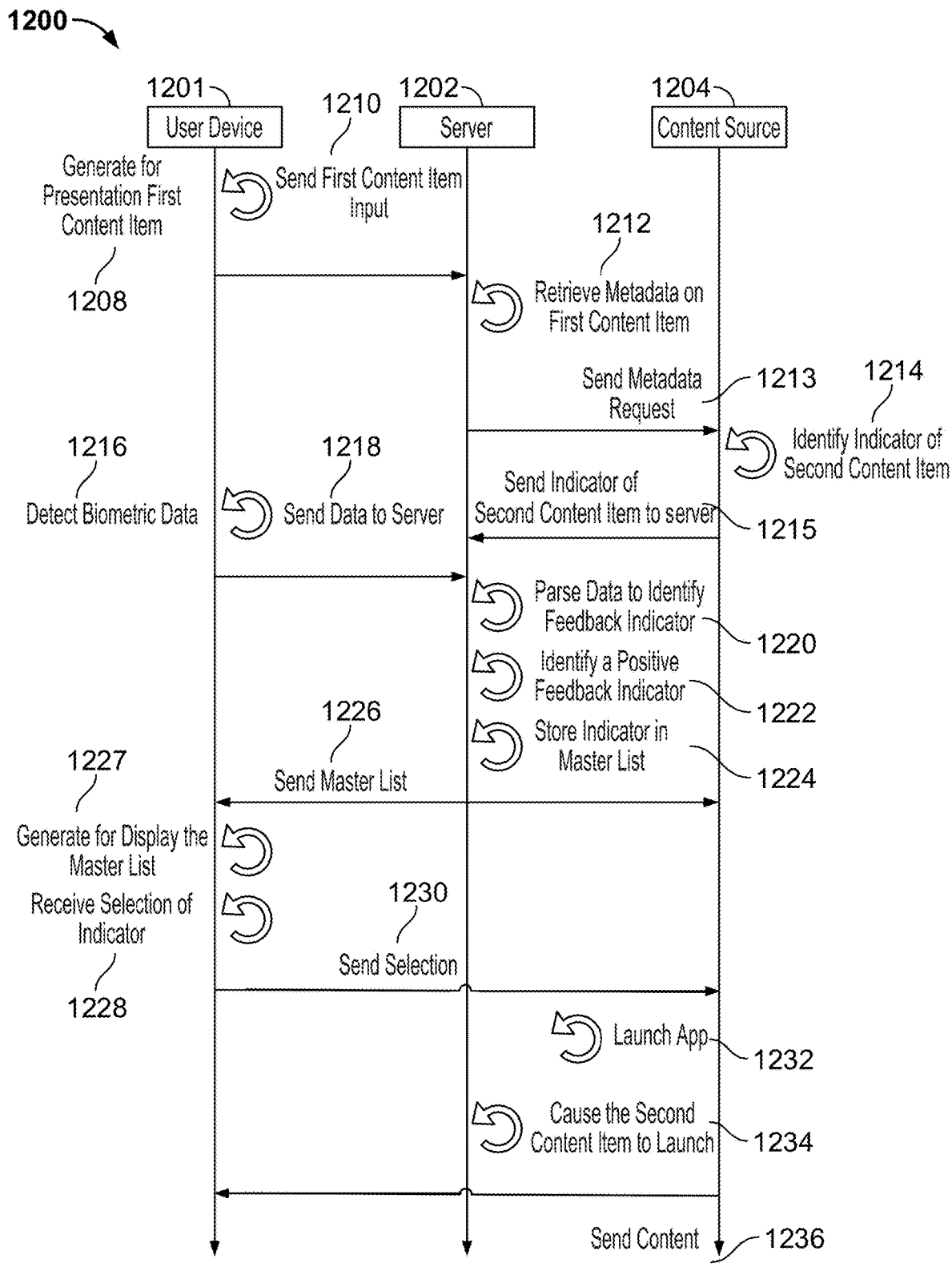
FIG. 12 is a flowchart of a detailed illustrative process for providing personalized content based on captured gestures, in accordance with some embodiments of the present disclosure.

FIG. 12 is a processing flow 1400 for providing, based on captured gestures, personalized content with a user device 1201, a server 1202 communicating with a user device and a content source 1204, in accordance with some embodiments of the present disclosure. It should be noted that process 1200 or any step thereof could be performed on, or provided by, the system of FIGS. 4 and 5 or any of the devices shown in FIGS. 1-3 and 11. In some embodiments, the steps of process 1200 are performed as described in the discussion of FIG. 1. For example, process 1200 may be executed by devices 502, 504, 508, or 510 (e.g., via control circuitry 404) and/or control circuitry of the vehicle system, as instructed by an authentication application that may be implemented on the user device 1201 and/or server 1202, and/or content source 1204, such as to distribute control of database management application operations for a target device among multiple devices. In addition, one or more steps of process 1200 may be incorporated into or combined with one or more steps of any other process or embodiment (e.g., process 700 of FIG. 7, process 800 of FIG. 8, process 900 of FIG. 9, process 1000 of FIG. 10 or process 1100 of FIG. 11).

At 1208, process circuitry may generate for presentation a first content item into the user device 1201. The first content item may be an advertisement for a media asset or a product. At 1210, the control circuitry of the user device 1201 may send the first content item via a communication network to server 1202. At 1212, the control circuitry of server 1202 may retrieve metadata on the first content item. Such metadata may include an identifier of a second content item that is associated with the first content item. For example, the first content item may be an advertisement (e.g., commercial for "Ozark") and the second content item may be the show, Ozark. At 1213, the control circuitry of server 1202 sends metadata request of the retrieved first content item to the control circuitry of content source 1204. The control circuitry of the content source 1204 may be in a server that operates as an OTT content source. In some embodiments, the control circuitry of the content source acquires the user data to confirm user accessibility to the content source. The metadata may include the first content item data. In some embodiments, instead of the data being sent in step 1213, a request may be transmitted to provide an indicator for the second content item.

At 1214, the control circuitry of the content source 1204, based on the metadata of the first content item, identifies an indicator of the second content item. Such an indicator may include content source metadata (e.g., content source name, second content item information, etc.). At 1215, the control circuitry of the content source 1204 transmits the indicator of the second content item to the control circuitry of the server 1202. At 1216, the control circuitry of the user device 1201 captures the user's biometric data in reaction to the first content item. For example, the vehicle system captures an image of the user providing feedback of a thumbs-up. Upon the capture of the user's feedback, at 1218, the control circuitry of the user device transmits the data to server 1202. For example, the user device sends biometric data to server 1202.

At 1220, the control circuitry of server 1202 parses the biometric data to identify feedback indicators. For example, as discussed above, the control circuitry divides up the data to identify a thumbs-up, thumbs-down, a heart, or any other suitable means of communication with hand gestures. In some embodiments, the control circuitry of server 1202, at 1222, identifies a positive feedback indicator (e.g., thumbs-up) from the biometric data. The control circuitry of the server 1202, at 1224, stores the indicator in a master list for access. The control circuitry of server 1202, at 1226, sends the master list to the user device. (In some embodiments, the sending of the master list to the user device may be optional, and the master list may be sent to the content source 1204 and stored directly). The control circuitry of the user device 1201, at 1227, generates the master list for display. At 1228, the control circuitry of the user device 1201 receives a selection of an indicator of a second content item, for example, "Ozark."

The control circuitry of the user device 1201 at 1230 sends the received selection to the content source. In response to the received selection, at 1232, the control circuitry of the content source 1204 launches the content source (e.g., Netflix) and, at 1234, causes the second content item (e.g., "Ozark") to launch for presentation. Separately, or in addition to 1234, at 1236, the control circuitry of the content source 1204 sends the data packet of the second content item to the user device for output.

As referred to herein, the terms "media asset", "content" and "content item" should be understood to mean an electronically consumable user asset, such as television programming, as well as pay-per-view programs, on-demand programs (as in video-on-demand (VOD) systems), internet content (e.g., streaming content, downloadable content, webcasts, etc.), a collection of episodes in a series, a single episode in a series, video clips, audio, content information, pictures, rotating images, documents, playlists, websites, articles, books, electronic books, blogs, advertisements, chat sessions, social media, chat rooms, applications, games, and/or any other media or multimedia and/or combination of the same. Guidance applications also allow users to navigate among and locate content. As referred to herein, the term "multimedia" should be understood to mean content that utilizes at least two different content forms described above, for example, text, audio, images, video, or interactivity content forms. Content may be recorded, played, displayed or accessed by user equipment devices, but can also be part of a live performance.

As referred to herein, the phrase "in response" should be understood to mean automatically, directly and immediately as a result of, without further input from the user, or automatically based on the corresponding action where intervening inputs or actions may occur.

The processes described above are intended to be illustrative and not limiting. One skilled in the art would appreciate that the steps of the processes discussed herein may be omitted, modified, combined, and/or rearranged, and any additional steps may be performed without departing from the scope of the invention. More generally, the above disclosure is meant to be exemplary and not limiting. Only the claims that follow are meant to set bounds as to what the present invention includes. Furthermore, it should be noted that the features and limitations described in any one example may be applied to any other example herein, and flowcharts or examples relating to one example may be combined with any other example in a suitable manner, done in different orders, or done in parallel. In addition, the systems and methods described herein may be performed in real-time. It should also be noted that the systems and/or methods described above may be applied to, or used in accordance with, other systems and/or methods.

What is claimed is:

1. A method comprising:
   monitoring, by a user device, user gestures to create a master list, wherein the master list stores, for each detected user gesture: (a) user feedback indicated by a respective user gesture, (b) an identifier of a first content item for which a respective user gesture was detected, and launchable application via which the first content item is available to be played at the user device;
   receiving user gesture data based on a first user gesture captured via a camera during output of a second content item via a second launchable application for receiving streaming data exclusively from a second streaming service provider, wherein the second content item is a recommendation for the first content item, wherein the first content item is available via the first launchable application for receiving streaming data exclusively from a first streaming service provider running on the user device;
   parsing, by control circuitry, the captured user gesture data to determine, as a feedback determination for the first content item, whether the user gesture indicates positive feedback or negative feedback;
   transmitting at least a portion of the second content item to at least one server, wherein the at least one server is configured to identify the first launchable application and metadata of the first content item based on metadata of the second content item;
   storing in the master list: (a) the feedback determined based on the first user gesture captured during the output, via the second launchable application, indicating the first content item, (b) an identifier of the first content item associated with the metadata of the first content item identified by the at least one server, and (c) the identifier of the first launchable application based on the identifying of the first launchable application by the at least one server;
   displaying, via a user interface, the master list;
   based at least on user selection of the identifier of the first content item displayed as part of the master list, launching the first launchable application; and generating for play, on the user device, the first content item in the first launchable application by retrieving, over the network, the first content item from the first streaming service provider.

2. The method of claim 1, further comprising:
in response to the user gesture data, generating a plurality of segments from the first content item, each segment of the plurality of segments being associated with metadata that identifies a content type and a second identifier of the segment;
generating for display a notification to provide additional feedback;
in response to generating for display the notification, causing capture, via the camera, a second user gesture during output of the segment of the plurality of segments of the first content item on the user device;
parsing, by the control circuitry, second user gesture data based on the captured second user gesture to identify a second feedback for the segment of the plurality of segments; and
in response to identifying that the second feedback is positive, storing in the master list the identifier of the segment of the plurality of segments of the first content item.

3. The method of claim 1, wherein the first content item is associated with a product; and the method further comprises:
retrieving product information associated with the product; and
in response to determining, based on the user gesture data, that the feedback is positive towards the product, adding the retrieved product information to a shopping list for purchase.

4. The method of claim 1, wherein the second content item is one of video content, audio content, game content, interactive content or textual content.

5. The method of claim 1, wherein the first streaming service provider is a broadcasting station, a television station, or content on-demand,
wherein the second streaming service provider is one of a broadcasting station, a television station, or content on-demand.

6. The method of claim 1, wherein the second content item is on-demand content, recorded content or live content.

7. The method of claim 1, wherein the capturing via sensors, comprises:
capturing, via a capture engine using sensors, data of a proximity of the user device;
creating a depth map to identify the user gesture during output of the second content item; and
the method further comprising identifying, using the control circuitry, feedback indicative of user intent from the depth map.

8. The method of claim 1, wherein the user gesture comprises one or more of a hand gesture of thumbs-up, a hand gesture of thumbs-down, a hand gesture of a heart, movement of a hand in a direction, movement of a finger, movement of an arm, movement of a palm of a hand, a first hand or a second hand of the user.

9. The method of claim 8, further comprising:
determining, using a machine learning model on the control circuitry, an intent of the user based on the user gesture during output of the second content item; and
responsive to the determined intent, retrieving for output the second content item from the second streaming service provider on the user device.

10. The method of claim 1, wherein the feedback indicator indicates the user gesture captured in reaction to the second content item.

11. The method of claim 10, wherein the feedback indicator indicates a thumbs up gesture.

12. The method of claim 1, wherein the feedback indicator describes the captured user gesture by showing a symbol representing the captured user gesture.

13. A system comprising:
input/output circuitry configured to:
receive user gesture data based on a user gesture captured via a camera during output of a recommendation for a first content item available via a first launchable application running on a user device for receiving streaming data exclusively from a first streaming service provider, wherein the output is of a second content item recommending the first content item, wherein the second content item is output via a second launchable application for receiving streaming data exclusively from a second streaming service provider; and
control circuitry configured to:
parse the user gesture data to determine, as a feedback determination for the first content item, whether the user gesture indicates positive feedback or negative feedback;
transmit at least a portion of the second content item to at least one server, wherein the at least one server is configured to identify the first launchable application and metadata of the first content item based on metadata of the second content item;
store in a master list: (a) the feedback determined based on the user gesture captured, (b) an identifier of the first content item identified by the at least one server, and (c) an identifier of the first launchable application based on the identifying of the first launchable application by the at least one server;
display, via a user interface, the master list;
based at least on user selection of the identifier of the first content item displayed as part of the master list, launch the first launchable application; and
generate for play, by the user device, the second content item in the first launchable application by retrieving, over the network, the first content item from the first streaming service provider.

14. The system of claim 13, the control circuitry is further configured to:
generate, in response to the receiving of the user gesture data, a plurality of segments from the first content item, each segment of the plurality of segments being associated with metadata that identifies a content type and a second identifier of the segment;
generate for display a notification to provide additional feedback;
in response to the generating for display of the notification, cause capture, via the input/output circuitry, at least one form of a second user gesture during output of the segment of the plurality of segments of the first content item on the user device;
parse, by the control circuitry, the captured second user gesture to identify a second feedback for the segment of the plurality of segments; and
in response to identifying that the second feedback indicator is positive, store in the master list the identifier of the segment of the plurality of segments of the first content item.

15. The system of claim 13, wherein the first content item is associated with a product; and the control circuitry is further configured to:
- retrieve product information associated with the product; and
- in response to determining, based on the user gesture data, that the feedback is positive towards the product, adding the retrieved product information to a shopping list for purchase.

16. The system of claim 13, wherein the second content item is one of video content, audio content, game content, interactive content or textual content.

17. The system of claim 13, wherein the first streaming service provider is a broadcasting station, a television station, or content on-demand,
- wherein the second streaming service provider is a broadcasting station, a television station, or content on-demand.

18. The system of claim 13, wherein the control circuitry is configured to capture via input/output circuitry by:
- capturing, via a capture engine using sensors, data of a proximity of the user device;
- creating a depth map to identify the user gesture during output for consumption of the second content item; and the system further comprises:
- identifying, using the control circuitry, the feedback indicative of user intent from the depth map.

* * * * *